United States Patent
Ying et al.

(10) Patent No.: US 12,006,513 B2
(45) Date of Patent: Jun. 11, 2024

(54) METHODS FOR THE LONG-TERM EXPANSION OF GRANULOCYTE-MACROPHAGE PROGENITORS AND APPLICATIONS THEREOF

(71) Applicant: University of Southern California, Los Angeles, CA (US)

(72) Inventors: Qi-Long Ying, Los Angeles, CA (US); Shi Yue, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 317 days.

(21) Appl. No.: 17/224,924

(22) Filed: Apr. 7, 2021

(65) Prior Publication Data

US 2021/0292712 A1 Sep. 23, 2021

Related U.S. Application Data

(63) Continuation of application No. PCT/US2019/055072, filed on Oct. 7, 2019.

(60) Provisional application No. 62/742,887, filed on Oct. 8, 2018.

(30) Foreign Application Priority Data

Jul. 12, 2019 (CN) .......................... 201910630151.8

(51) Int. Cl.
*C12N 5/0786* (2010.01)
*C12N 5/0787* (2010.01)

(52) U.S. Cl.
CPC ......... *C12N 5/0645* (2013.01); *C12N 5/0642* (2013.01); *C12N 2500/25* (2013.01); *C12N 2500/30* (2013.01); *C12N 2500/84* (2013.01); *C12N 2501/10* (2013.01); *C12N 2501/22* (2013.01); *C12N 2501/415* (2013.01); *C12N 2501/999* (2013.01); *C12N 2510/00* (2013.01)

(58) Field of Classification Search
None
See application file for complete search history.

(56) References Cited

U.S. PATENT DOCUMENTS

| | | |
|---|---|---|
| 2013/0273649 A1 | 10/2013 | Wu et al. |
| 2014/0377234 A1 | 12/2014 | Fong et al. |
| 2017/0275593 A1 | 9/2017 | Hanna et al. |
| 2020/0080059 A1* | 3/2020 | Thomson ............. C12N 5/0647 |
| 2022/0177842 A1* | 6/2022 | Tong .................... C12N 5/0647 |

FOREIGN PATENT DOCUMENTS

WO WO-2017180694 A1 * 10/2017 ............. C07K 19/00

OTHER PUBLICATIONS

Eliason JF. Granulocyte-macrophage colony formation in serum-free culture: effects of purified colony-stimulating factors and modulation by hydrocortisone. J Cell Physiol. Aug. 1986;128(2):231-8. doi: 10.1002/jcp.1041280214. PMID: 3488320. (Year: 1986).*
Alvey CM, Spinler KR, Irianto J, Pfeifer CR, Hayes B, Xia Y, Cho S, Dingal PCPD, Hsu J, Smith L, Tewari M, Discher DE. SIRPA-Inhibited, Marrow-Derived Macrophages Engorge, Accumulate, and Differentiate in Antibody-Targeted Regression of Solid Tumors. Curr Biol. Jul. 24, 2017;27(14):2065-2077.e6. (Year: 2017).*
B-27 serum-free supplement (50x) liquid. Thermo Fisher Scientific—US. (n.d.). Retrieved May 4, 2023, from https://www.thermofisher.com/us/en/home/technical-resources/media-formulation.250.html (Year: 2020).*
Thomas, Shane, International Search Report & Written Opinion, United States Patent & Trademark Office, PCT/US2019/055072, dated Dec. 30, 2019.
Nickitas-Etienne, Athina, International Preliminary Report on Patentability and Written Opinion, The International Bureau of WIPO, PCT/US2019/055072, dated Apr. 22, 2021.

* cited by examiner

*Primary Examiner* — Allison M Fox
*Assistant Examiner* — Alyssa G Weston
(74) *Attorney, Agent, or Firm* — Parker Highlander PLLC

(57) ABSTRACT

The disclosure provides methods for the long-term expansion of granulocyte-macrophage progenitors, the granulocyte-macrophage progenitors generated therefrom, and uses of the granulocyte-macrophage progenitors thereof.

22 Claims, 27 Drawing Sheets
(2 of 27 Drawing Sheet(s) Filed in Color)

D

E

A

METHODS FOR THE LONG-TERM EXPANSION OF GRANULOCYTE-MACROPHAGE PROGENITORS AND APPLICATIONS THEREOF

CROSS REFERENCE TO RELATED APPLICATIONS

This application is a continuation of International Application Number PCT/US2019/055072, filed Oct. 7, 2019, which application claims priority under 35 U.S.C. § 119 from Provisional Application Ser. No. 62/742,887, filed Oct. 8, 2018, and Chinese Application No. 201910630151.8, filed Jul. 12, 2019, the disclosures of which are incorporated herein by reference.

TECHNICAL FIELD

The disclosure provides methods for the long-term expansion of granulocyte-macrophage progenitors, the granulocyte-macrophage progenitors generated therefrom, and uses of the granulocyte-macrophage progenitors thereof.

BACKGROUND

Granulocytes, macrophages, and dendritic cells are the essential components of the innate immune system in humans. They are the first line of defense against pathogens and also play a central role in maintaining the homeostasis of our body and preventing various diseases including infection, metabolic diseases and cancer. These cells originate from a common progenitor in the bone marrow, the granulocyte-macrophage progenitor (GMP).

SUMMARY

Provided herein are methods that allow for the expansion of granulocyte/macrophage progenitors (GMPs), e.g., the long-term and clonal expansion of GMPs. These methods are generally applicable in generating long-term and clonal expansion of GMPs from any number of subject sources, including from mice, rats, humans, etc. In some embodiments, one of the many advantages of the GMPs generated by the methods of the disclosure, is that the GMPs are susceptible to genetic modification techniques, thereby allowing for the use of the GMPs in basic scientific research and clinical therapeutic applications. Thus, expanded and genetically modified GMPs can be readily translated into broad clinical applications. For example, human GMPs can be genetically modified so that they differentiate into macrophages (e.g. knockout SIRPα and/or PI3Kγ gene). These engineered macrophages may or are expected to have enhanced antitumor effects and can be used clinically to treat cancer, either as monotherapy or combination therapy with other immunological agents, such as anti-PD-1/PD-L1 antibodies and chimeric antigen receptor T (CAR-T) cells. In addition, ex vivo expanded human GMPs can be readily used for infusion or transplantation to treat neutropenia cause by, for example, chemotherapy, radiotherapy and the like. Such ex vivo expanded GMPs can be autologous or allogeneic to the subject.

The disclosure provides a method for the expansion of a population of granulocyte/macrophage progenitor cells (GMPs), comprising culturing GMPs in a culture medium comprising: (i) a growth factor, (ii) a B-Raf kinase inhibitor, and (iii) a Wnt activator and/or a GSK-3 inhibitor, wherein, the GMPs remain substantially morphologically unchanged after undergoing multiple cell passages and/or clonal expansion. In one embodiment, the GMPs are derived or obtained from stem cells. In a further embodiment, the stem cells are genetically engineered prior to or during culturing. In yet another or further embodiment, the stem cells are hematopoietic stem cells. In yet another or further embodiment, the hematopoietic stem cells are isolated from the bone marrow of a subject. In a further embodiment, the subject is a mammalian subject. In yet another or further embodiment, the subject is a human, a rat or a mouse. In yet another or further embodiment, the culture medium comprises DMEM/F12 and Neural Basal Medium. In yet another or further embodiment, the culture medium comprises DMEM/F12 and Neural Basal Medium in a ratio of about 5:1 to about 1:5. In yet another or further embodiment, the culture medium comprises DMEM/F12 and Neural Basal Medium in a ratio of about 1:1. In yet another or further embodiment, the culture medium comprises one or more supplements selected from insulin, transferrin, BSA fraction V, putrescine, sodium selenite, DL-α tocopherol, and/or linolenic acid. In yet another or further embodiment, the culture medium is supplemented with insulin, transferrin, BSA fraction V, putrescine, sodium selenite, DL-α tocopherol, and linolenic acid. In yet another or further embodiment, the growth factor is stem cell factor (SCF). In yet another or further embodiment, the B-Raf kinase inhibitor is selected from GDC-0879, PLX4032, GSK2118436, BMS-908662, LGX818, PLX3603, RAF265, RO5185426, vemurafenib, PLX8394, SB590885 and any combination thereof. In yet another or further embodiment, the B-Raf kinase inhibitor is GDC-0879. In yet another or further embodiment, the Wnt activator is selected from SKL 2001, BML-284, WAY 262611, CAS 853220-52-7, QS11 and any combination thereof. In yet another or further embodiment, the Wnt activator is SKL 2001. In yet another embodiment of any of the foregoing embodiments, the GSK-3 inhibitor is selected from CHIR99021, CHIR98014, SB216763, BIO, A1070722, AR-A014418 and any combination thereof. In yet another or further embodiment, the GSK-3 inhibitor is CHIR99021. In yet another or further embodiment, the GMPs have the uniform morphology of being small, round-shaped, and/or non-adherent.

The disclosure also provides a method to genetically modify granulocyte/macrophage progenitor (GMPs) cells, comprising genetically engineering a modification into GMPs made by any of the foregoing methods using a gene editing system, homologous recombination, or site directed mutagenesis. In one embodiment, the gene editing system is a TALEN- or CRISPR-based system. In yet another or further embodiment, the genetically engineering modification comprises replacing or disrupting an existing gene (knockout), or altering a genetic locus to contain sequence information not found at the genetic locus (knock-in). In yet another or further embodiment, the genetically engineering modification of the GMPs comprises a knockout SIRPα and/or PI3Kγ gene. In another embodiment, of any for the foregoing, the method further comprises differentiating the GMPs into macrophages comprising culturing the GMPs with a macrophage differentiation medium comprising macrophage colony-stimulating factor (MCSF). In one embodiment, the macrophage differentiation medium comprises RPMI 1640, fetal bovine serum (FBS) and MCSF. In yet another or further embodiment, the differentiation medium comprises RPMI 1640, 10% FBS and 20 ng/mL of MCSF. In yet another or further embodiment of any of the foregoing, the method further comprises differentiating the GMPs into granulocytes comprising culturing the GMPs with a granulocyte differentiation medium comprising granulocyte colony-stimulating factor (GCSF). In yet another or further embodiment, the granulocyte differentiation medium comprises RPMI 1640, FBS and GCSF. In yet another or further embodiment, the granulocyte differentiation medium comprises RPMI 1640, 10% FBS and 20 ng/mL of GCSF.

The disclosure also provides a population of granulocyte/macrophage progenitor cells (GMPs) expanded by a method of the disclosure.

The disclosure also provides genetically modified granulocyte/macrophage progenitor cells (GMPs) prepared by a method of the disclosure.

The disclosure provides macrophages prepared by a method of the disclosure.

The disclosure provides granulocytes prepared by a method of the disclosure.

The disclosure also provides a pharmaceutical composition comprising an effective amount of the population of the GMPs, the genetically modified GMPs, macrophages, or granulocytes made by the methods disclosed herein, and a pharmaceutically acceptable carrier or excipient.

The disclosure also provides a method for treating or preventing a disease or condition in a subject in need comprising administering to said subject an effective amount of the population of the GMPs, the genetically modified GMPs, macrophages, or granulocytes made by the methods of the disclosure, and a pharmaceutically acceptable carrier or excipient.

The disclosure also provides for the use of an effective amount of the population of the GMPs, the genetically modified GMPs, macrophages, or granulocytes of the disclosure in the manufacture of a medicament for treating or preventing a disease or condition in a subject in need.

DESCRIPTION OF DRAWINGS

The patent or application file contains at least one drawing executed in color. Copies of this patent or patent application publication with color drawing(s) will be provided by the Office upon request and payment of the necessary fee.

Figure 6A:
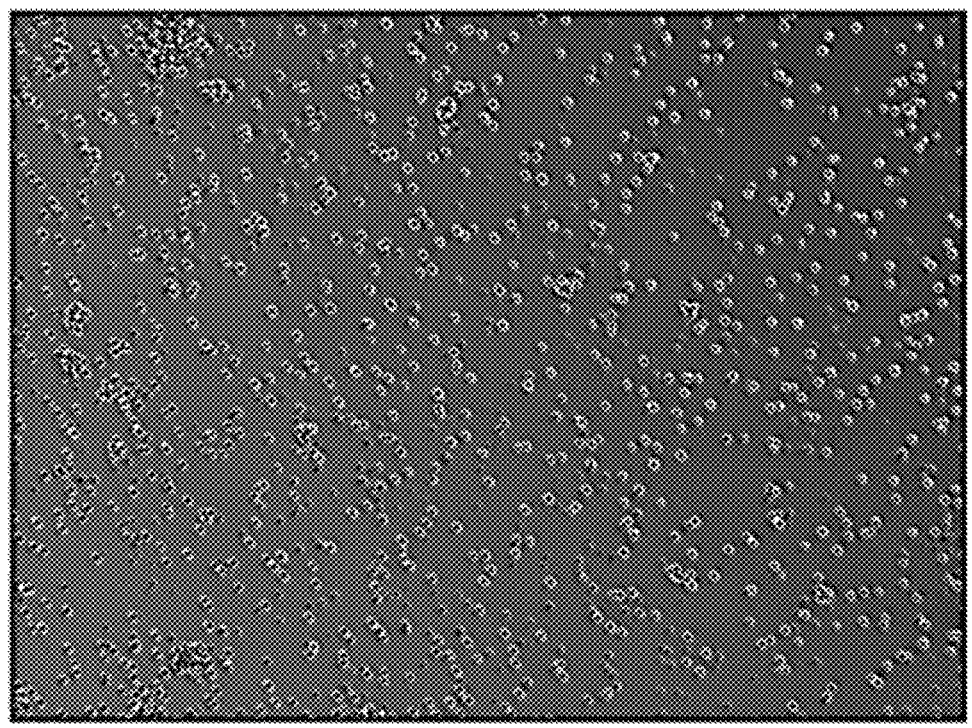
Figure 6A:
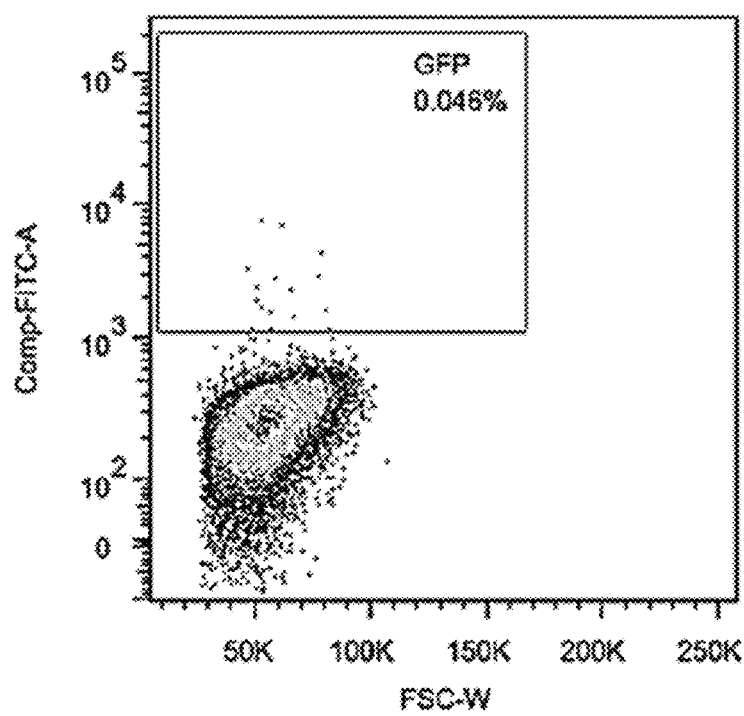
Figure 6A:
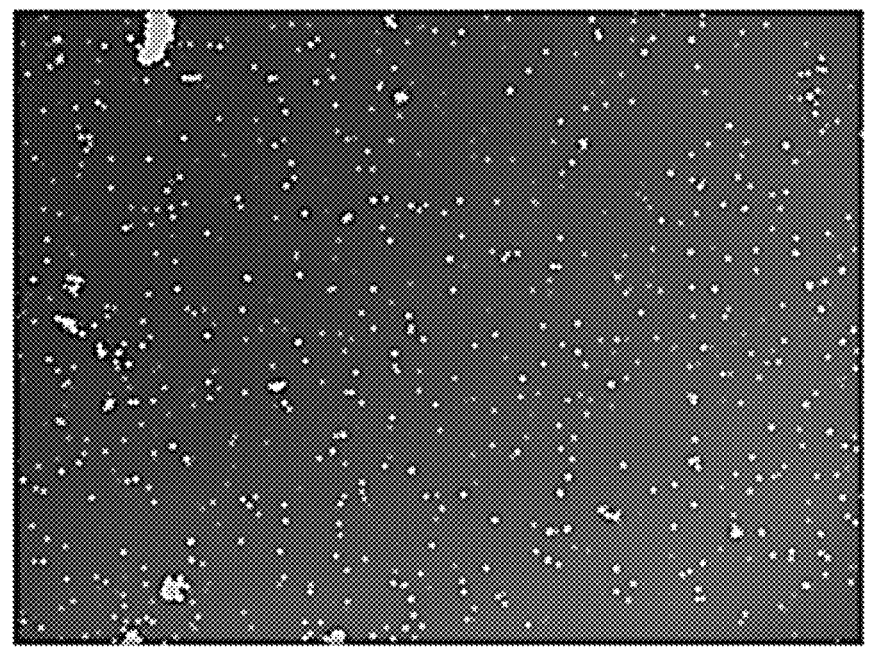
Figure 6A:
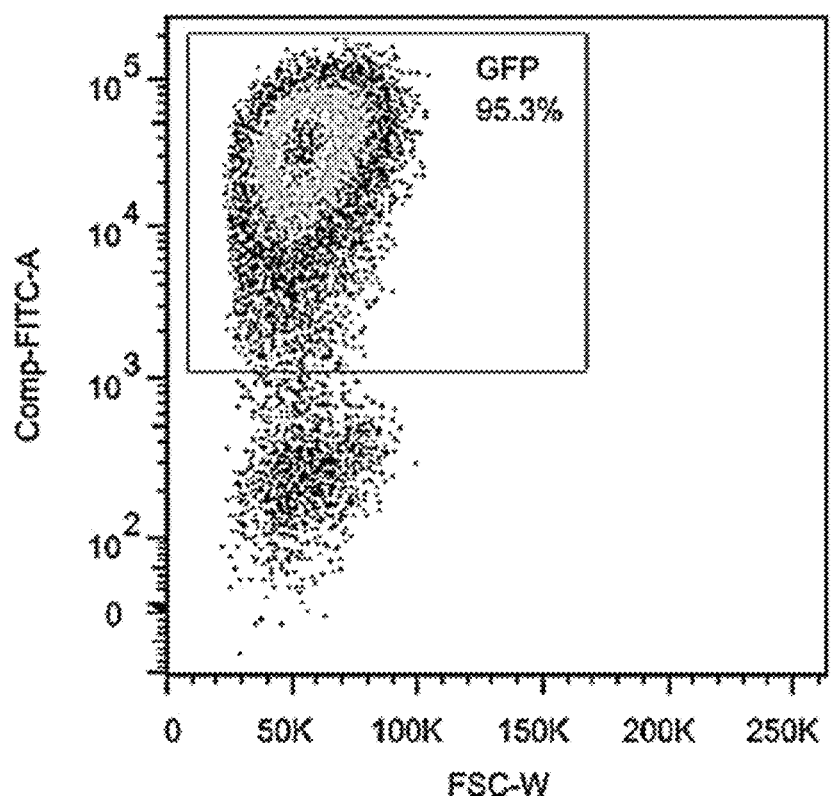
Figure 6B:
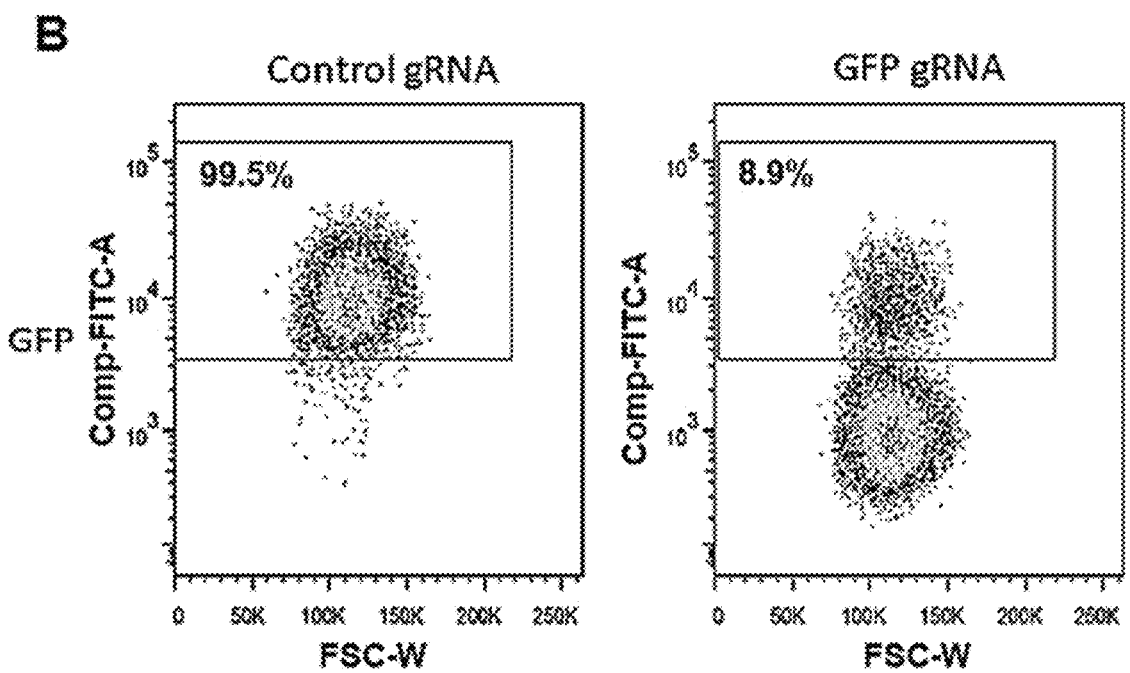
Figure 6C:
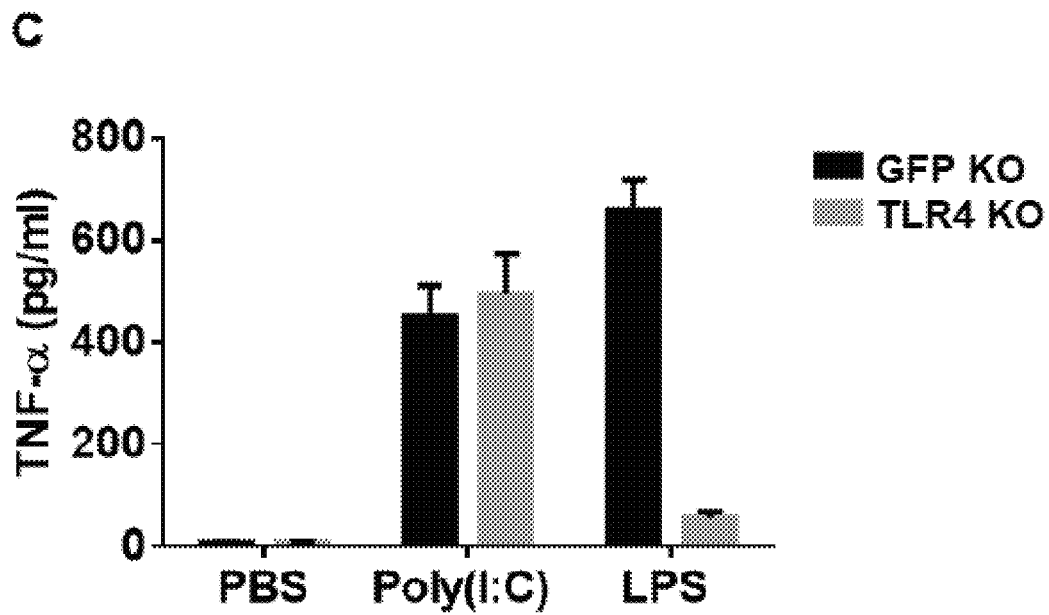
Figure 6C:
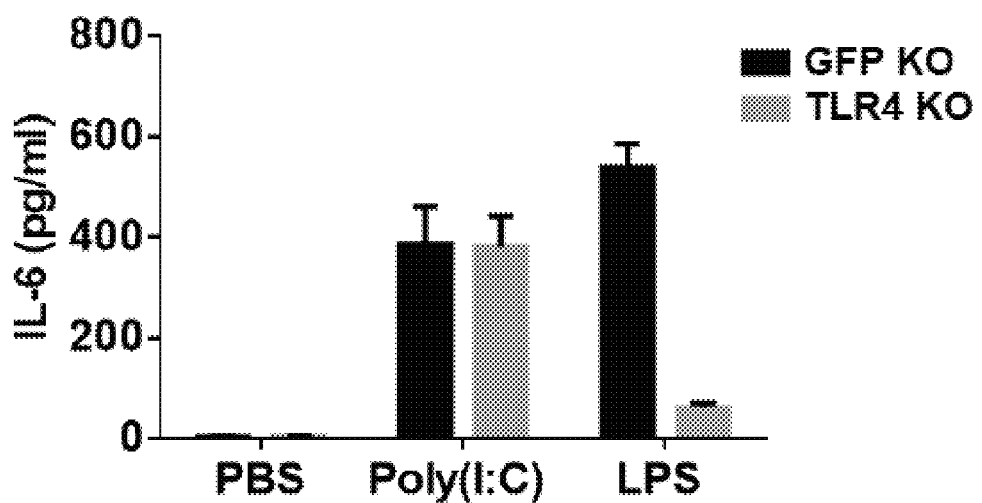
Figure 6C:
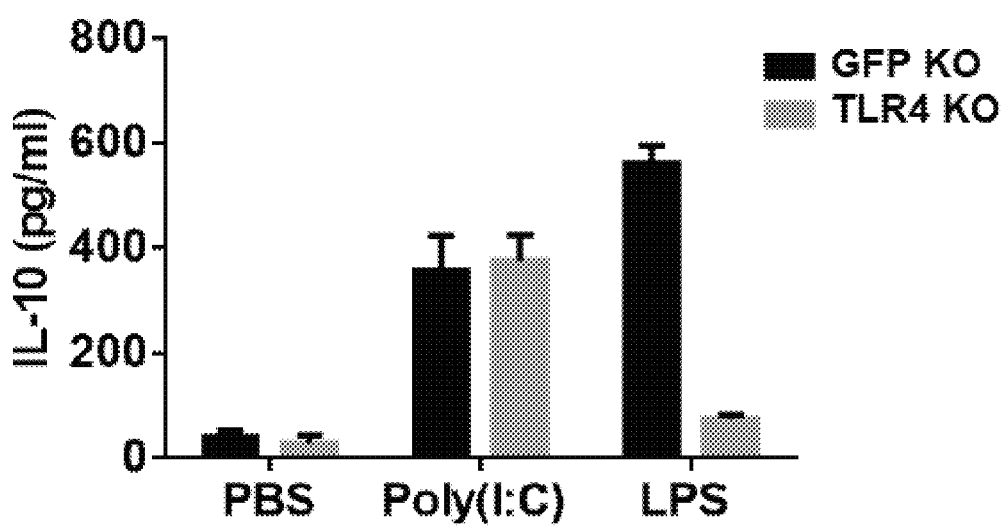
Figure 7A:
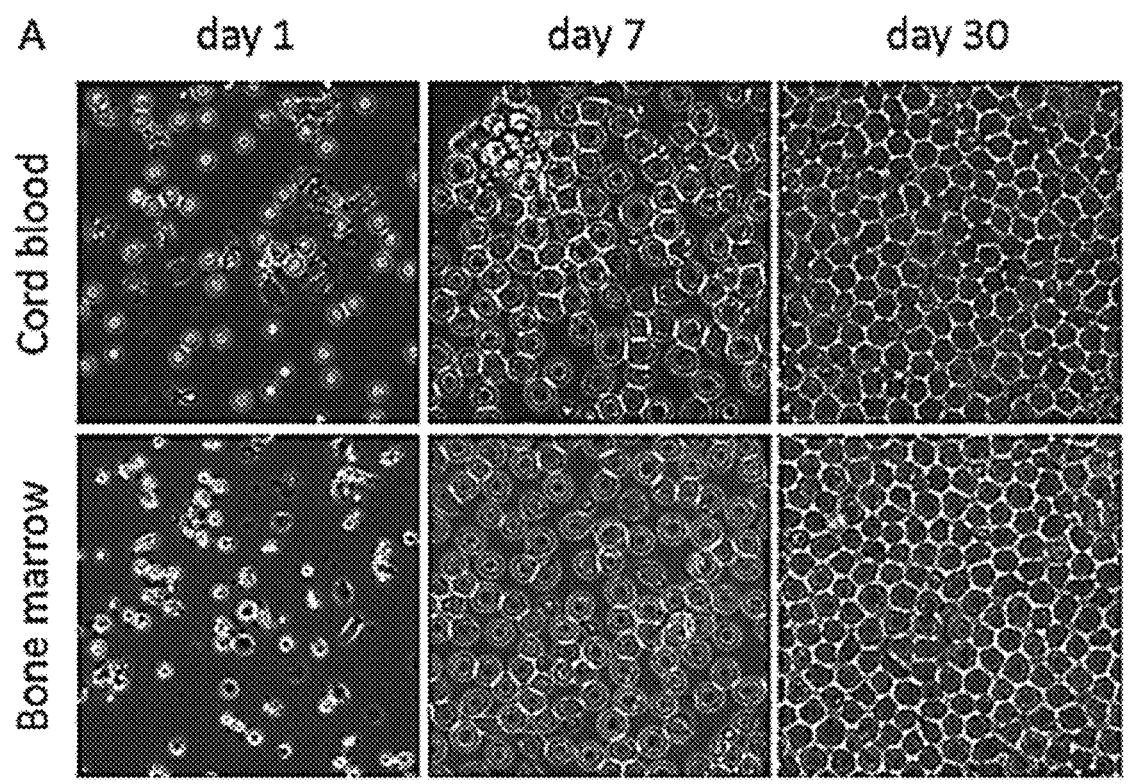
Figure 7B:
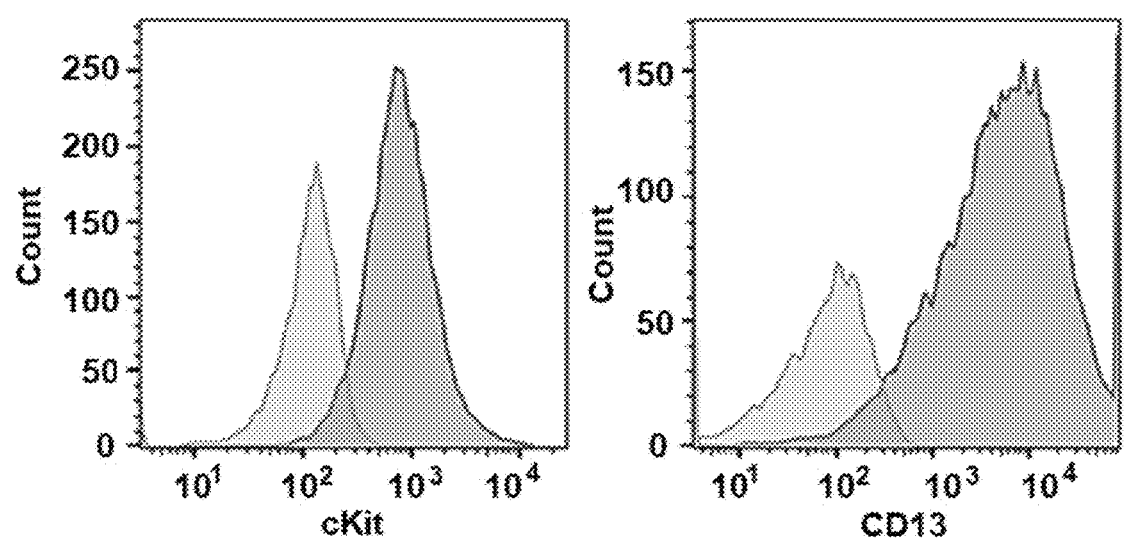
Figure 7B:
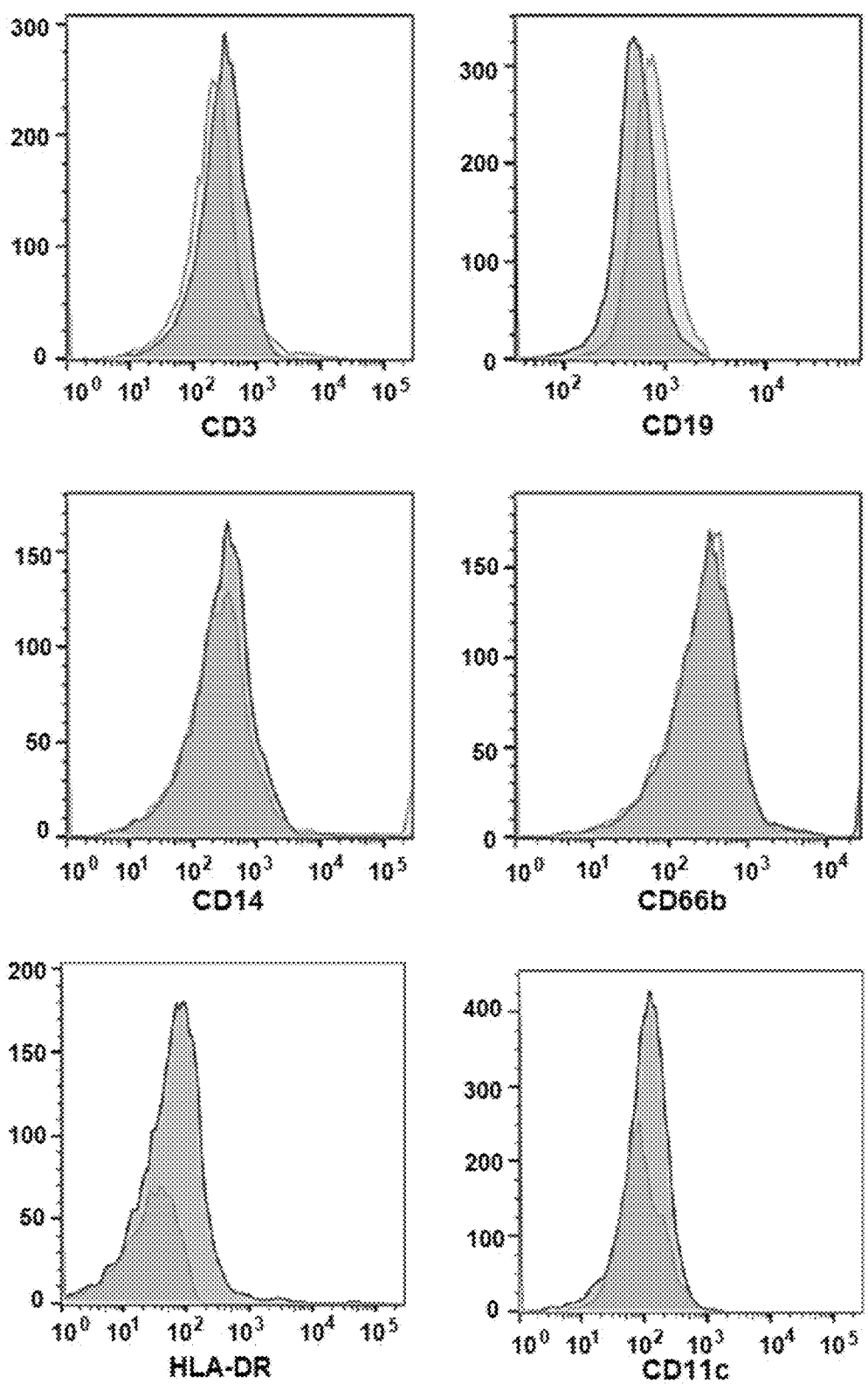
Figure 7C:
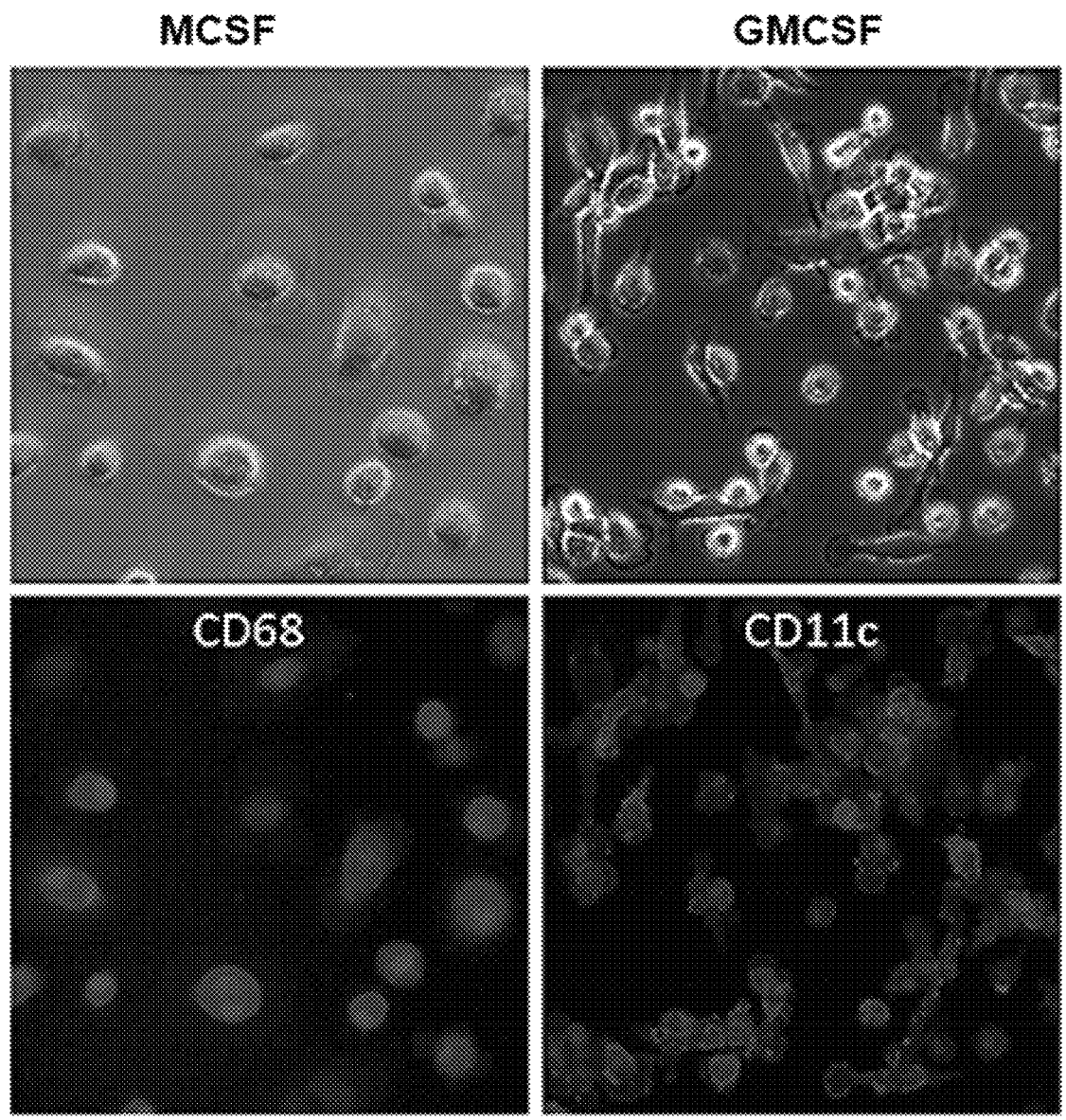
Figure 7D:
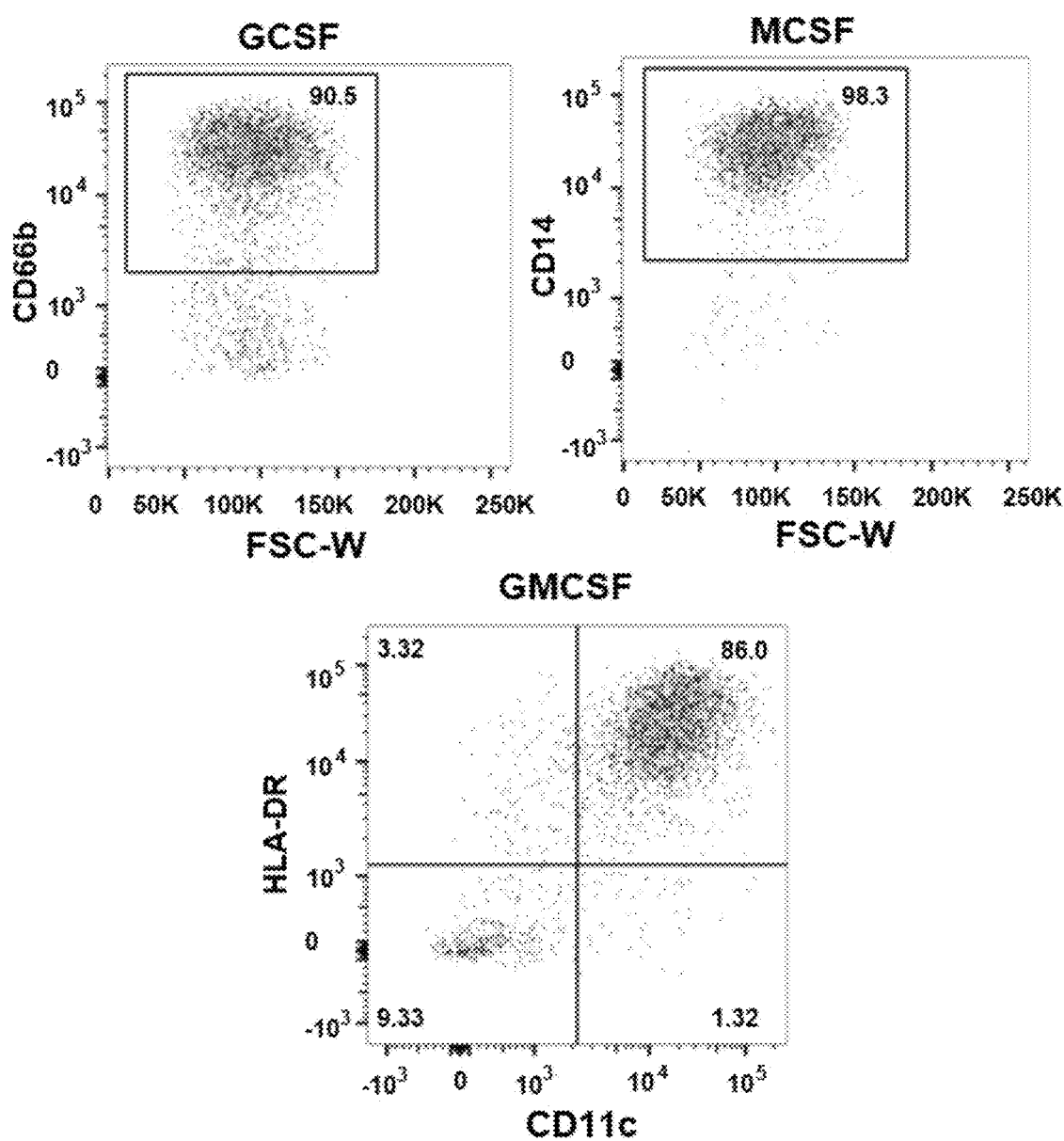
Figure 7E:
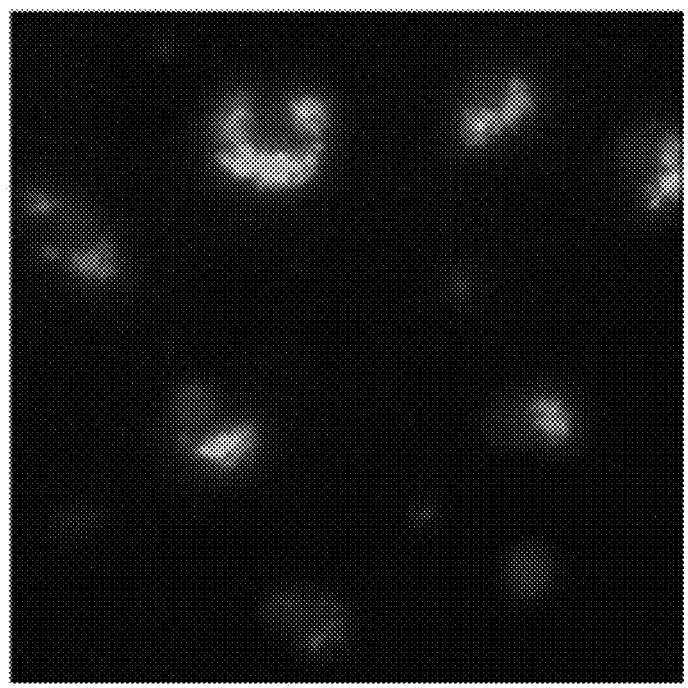
Figure 7F:
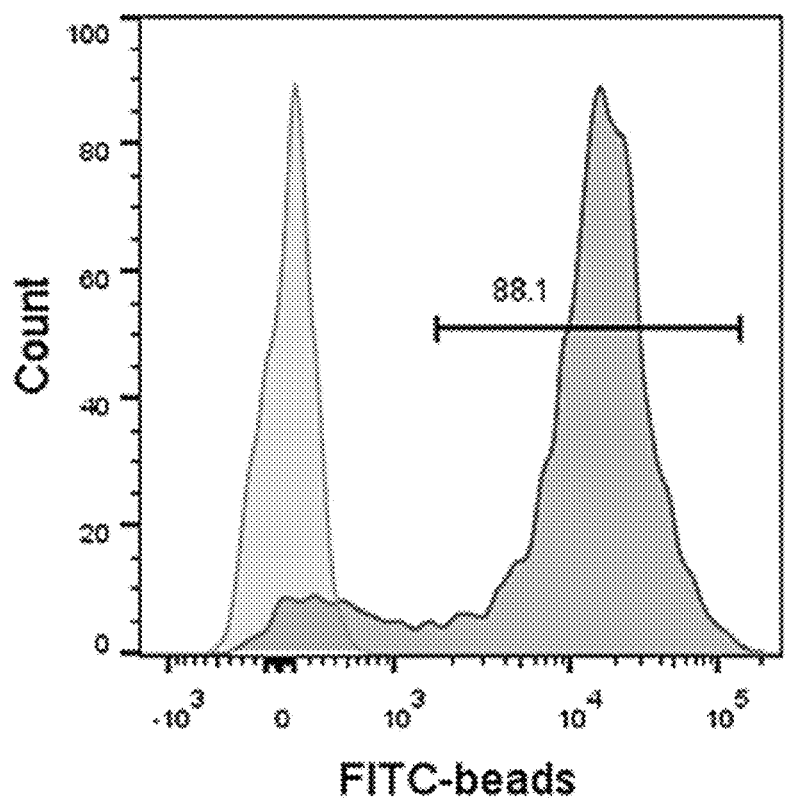

FIG. 6A-C provides for genetic modification of ex vivo expanded GMPs. (A) Transfection efficiency of GMPs transfected with GFP mRNA. More than 95% of GMPs transfected with GFP mRNA were GFP positive. (B) gRNAs targeting GFP were transfected into GMPs derived from the ROSA 26-CAG-Cas9-GFP mouse. About 91.1% of the GMPs transfected with GFP gRNAs became GFP negative 48 h after transfection. (C) gRNAs targeting TLR4 were transfected into GMPs, and then these GMPs were induced to differentiate toward mature macrophages, which were stimulated with Poly I:C and LPS. 24 h later the supernatant was harvested and the inflammatory cytokines secretion was measured by ELISA.

FIG. 7A-F provides for the long-term expansion and characterization of human GMPs. (A) Images of cell morphology after long term culturing in SCF/2i medium. $1 \times 10^6$ fresh human cord blood cells or bone marrow cells were plated into 1 well of the 12-well plate in SCF/2i medium. Cells were harvested and passaged every 3-4 days. (B) Presents flow cytometry data of cell surface markers. Lin–cKit+ CD13+. (C) Presents images demonstrating macrophage and dendritic cell differentiation. Human GMPs were cultured in RPMI 1640+10% FBS+20 ng/mL MCSF or GMCSF for 7 days. Mature macrophages and dendritic cells were re-plated, fixed and stained for CD68 and CD11c. (D) Presents the flow cytometry data of human GMPs derived neutrophils, macrophages and dendritic cells. Human GMPs were cultured in RPMI 1640+10% FBS+20 ng/mL GSCF for 4 days, or cultured in RPMI 1640+10% FBS+20 ng/mL MCSF or GMCSF for 7 days. Mature neutrophils, macrophages and dendritic cells were stained with CD66b, CD14, CD11b and HLA-DR and analyzed by flow cytometry. (E-F) Provides images of an in vitro functional test of ex vivo expanded human GMP-derived macrophages. FITC labeled latex beads were co-cultured with human GMP-derived macrophages for 1 h. Green: FITC-beads. Blue: nuclear. (E), cells were fixed and stained with DAPI, pictures were taken using Keyence microscope. (F), cells were harvested and FITC positive cells were analyzed by using BD Arial flow cytometry.

DETAILED DESCRIPTION

As used herein and in the appended claims, the singular forms "a," "an," and "the" include plural referents unless the context clearly dictates otherwise. Thus, for example, reference to "a cell" includes a plurality of cells and reference to "the granulocyte-macrophage progenitor" includes reference to one or more granulocyte-macrophage progenitors and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

It should be understood that this invention is not limited to the particular methodology, protocols, and reagents, etc., described herein and as such may vary. The terminology used herein is for the purpose of describing particular embodiments only and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

Granulocytes, macrophages, and dendritic cells originate from a common progenitor in the bone marrow, the granulocyte-macrophage progenitor (GMP). Despite the immense therapeutic potential of innate immune cells, their application in the clinic has been greatly limited because of the current inability to effectively expand and genetically modify these cells or their progenitors GMPs. Provided herein are methods for the long-term expansion of mouse and human GMPs. These conditions can likely also be used for the expansion of GMPs derived from other species. Ex vivo expanded GMPs can efficiently differentiate into mature and functional granulocytes, macrophages, and dendritic cells both in vitro and in vivo. These ex vivo expanded GMPs can also be genetically modified. The methods disclosed herein for the production of GMPs, and the GMPs produced therefrom, have great utility because: (1) long-term expansion of human GMPs provide unlimited homogenous cell populations for both basic research and clinical applications; (2) long-term expansion of human GMPs allows for the studying the regulation of an immune response by modifying GMP genes, and their expression thereof; and (3) Ex vivo expanded human GMPs can be used for clinical applications, including transplantation. For example, ex vivo expanded human GMPs can readily be used to treat neutropenia. Moreover, the disclosure provides for the genetic modification of human GMPs (e.g., knockout SIRPα and/or PI3Kγ gene; overexpression of angiotensin converting enzyme), which can be further induced to differentiate into macrophages and dendritic cells. These engineered macrophages and dendritic cells are expected to have enhanced antitumor effects and can be used clinically to treat cancer, either as monotherapy or combination therapy with other immunological agents, such as anti-PD-1/PD-L1 antibodies and chimeric antigen receptor T (CAR-T) cells. Human GMPs can also be engineered to produce CAR-macrophages, which can be used for the development of new treatments for cancer and other diseases.

Macrophages display divergent phenotypes that were originally classified as M1 or M2 polarity. M1 polarized macrophages display the capacity to present antigen, produce IL-12, IL-23, interferon gamma (IFNγ), and reactive oxygen species (ROS). M1 macrophages are more effective at antitumor and skewing T cell responses toward a T helper type 1 (Th1) or cell mediated immune response. In contrast, M2 macrophages produce IL-10 and TGF-β and participate in tissue remodeling, have immunosuppressive qualities, and promote Th2 or antibody mediated immune responses. Tumor-associated macrophages (TAMs) constitute a major component of the tumor microenvironment. These cells are predominant M2 phenotype macrophages which promote tumor immunosuppression. Recent studies support their contribution to the suppression of T cell function, which is not abolished by the use of Immune checkpoint blockage. Macrophages have therefore become an attractive therapeutic target to combat cancer. Despite the huge therapeutic potential of macrophages, their application in clinic has been greatly limited because currently there is no effective method to expand and genetically modify macrophages or their progenitors GMPs. Long-term expansion of human GMPs allows for genetic modification to make these cells more therapeutically applicable.

Figure 1A:
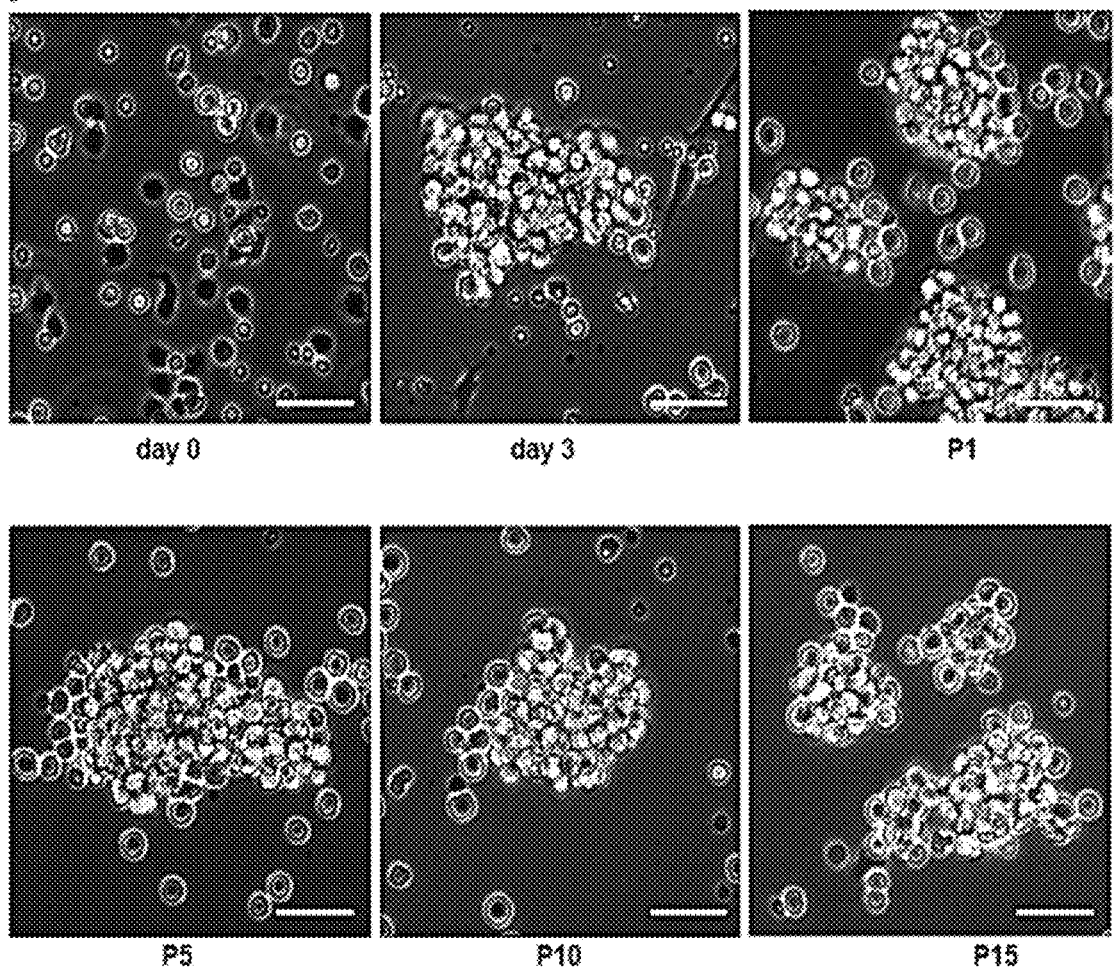
FIG. 1A-C shows the long-term culture of mouse GMPs. (A) Images of cell morphology after long term culturing in SCF/2i medium. $1×10^5$ fresh bone marrow cells were plated into 1 well of 12-well plate in SCF/2i medium. GMP colonies formed after 3 days, the colonies were harvested, trypsinized and passaged every 2-3 days. Representative images show the GMP colonies after different passage numbers. Scale bar:200 μm. (B) Images of cell morphology using different culture conditions. To determine whether SCF (F), GDC (G), and SKL (S) are important for the expansion of GMPs, $1×10^5$ fresh bone marrow cells were seeded in basal medium (N2B27) supplemented with the indicated inhibitors or growth factors. Representative pictures were taken on day 3 after plating. Scale bar: 200 um. (C) Presents an extended Cell growth curve of cells grown under different culture conditions. $1×10^5$ fresh bone marrow cells were cultured in the indicated conditions. Suspension cells were counted and passaged every 2 days. G: GDC0879; S: SKL2001; F: SCF.

It was found that inhibition of two protein kinases, the mitogen-activated protein kinase kinase (MEK) and glycogen synthase kinase 3 (GSK3), allows long-term self-renewal of mouse and rat embryonic stem cells (ESCs). Based on this finding, it was postulated that many, if not all, types of stem cells can be maintained during long-term in vitro culture by inhibiting signaling pathways responsible for initiating differentiation. In an attempt to identify inhibitors that can promote self-renewal of stem/progenitor cells of the hematopoietic system, bone marrow cells isolated from adult C57BL/6 mice were plated into 96-well plates in serum free N2B27 medium and then screened with small molecule libraries. A B-Raf kinase inhibitor (GDC-0879) was identified that could significantly promote the formation of colonies containing uniform bright, small and round-shaped cells. After passaging, however, these cells gradually attached and differentiated. Accordingly, another round screening was performed. The second screening identified a Wnt activator (SKL2001) that acted synergistically with GDC0879 to promote the expansion of the uniform round-shaped cells. The combination of GDC and SKL, however, was not found to be sufficient for the long-term expansion of the cells. A third screen was performed. In this screen, a panel of growth factors were identified as possibly being important for the long-term expansion of the cells. After further experimentation, it was found that methods which utilized stem cell factor (SCF) in combination with the B-Raf kinase inhibitor (GDC-0879) and the Wnt activator (SKL2001) allowed for the production of a uniform cell population of bright, small and round-shaped cells which could further undergo long term cell expansion (e.g., see FIG. 1A). The foregoing combination (SCF+GDC-0879+ SKL2001) is referred herein as SCF/2i. Thus, in various embodiments presented herein, methods of the disclosure utilize SCF with a B-Raf kinase inhibitor (GDC-0879) and a Wnt activator (SKL2001) to promote the long-term expansion of GMPs. In yet a further embodiment, the methods of the disclosure utilize SCF/2i to promote the long-term expansion of mouse and other GMPs. In an alternate embodiment, the methods of the disclosure utilize a combination of SCF with GDC-0879 and a GSK3 inhibitor (CHIR99021) to promote the long-term expansion of human and other GMPs.

In a particular embodiment, the disclosure provides a method for the long-term expansion of a uniform cell population of granulocyte/macrophage progenitor cells (GMPs) that remain morphologically unchanged after undergoing multiple cell passages and clonal expansion. In a further embodiment, a method disclosed herein comprises the step of culturing GMPs in a culture medium which includes a combination of factors and agents including, but not limited to, a growth factor (e.g., SCF), a B-Raf kinase inhibitor (e.g., GDC-0879), and a Wnt activator (e.g., SKL 2001) and/or a GSK-3 inhibitor (e.g., CHIR99021).

As used herein a "substantially uniform population" refers to a population of cells in which at least 80% of the cells are of the indicated type, preferably at least 90%, 95%, or even 98% or more.

As used herein a "long term culture" or "long term expansion" refers to the propagation of cells under controlled conditions such that the cells expand in number and/or maintain substantial viability and substantially similar morphology. In some embodiments the term refers to the time period of culture while maintaining a desired morphology and cell number (e.g., for about two months or longer) or may be associated with the number of passages (e.g., media changes) of at least 10 media passages. In other embodiments the term refers to the increase in number over a period of time (e.g., an increase by at least one million times in a about a two month period). In some embodiments, the long-term cultures are cultured for more than 4 months, more than 6 months or more than 1 year. In other embodiments, the long-term cultures are passaged for more than 15 passages, more than 18 passages or more than 20 passages.

In a further embodiment, the GMPs disclosed herein are derived from stem cells. Stem cells can include embryonic stem cells, induced pluripotent stem cells, non-embryonic (adult) stem cells, and cord blood stem cells. Stem cell types that can be cultured using the media of the disclosure include stem cells derived from any mammalian species including humans, mice, rats, monkeys, and apes (see, e.g., Nature, 448:313-318, July 2007; and Takahashi et al., Cell, 131(5): 861-872; which are incorporated herein by reference).

In a particular embodiment, the GMPs of the disclosure are derived from induced pluripotent stem cells (iPSs, or iPSCs). iPSCs are a type of pluripotent stem cell obtained from non-pluripotent cells by selective gene expression (of endogenous genes) or by transfection with a heterologous gene. Induced pluripotent stem cells are described by Shinya Yamanaka's team at Kyoto University, Japan. Yamanaka had identified genes that are particularly active in embryonic stem cells, and used retroviruses to transfect mouse fibroblasts with a selection of those genes. Eventually, four key pluripotency genes essential for the production of pluripotent stem cells were isolated; Oct-3/4, SOX2, c-Myc, and Klf4. Cells were isolated by antibiotic selection for Fbx15$^+$ cells. The same group published a study along with two other independent research groups from Harvard, MIT, and the University of California, Los Angeles, showing successful reprogramming of mouse fibroblasts into iPS and even producing a viable chimera.

In an alternate embodiment, the GMPs disclosed herein are derived from embryonic stem cells (ESCs). ESCs are stem cells derived from the undifferentiated inner mass cells of a human embryo. Embryonic stem cells are pluripotent, meaning they are able to grow (i.e. differentiate) into all derivatives of the three primary germ layers: ectoderm, endoderm and mesoderm. Pluripotency distinguishes embryonic stem cells from adult stem cells found in adults; while embryonic stem cells can generate all cell types in the body, adult stem cells are multipotent and can produce only a limited number of cell types. Additionally, under defined conditions, embryonic stem cells are capable of propagating themselves indefinitely. This allows embryonic stem cells to be employed as useful tools for both research and regenerative medicine, because they can produce limitless numbers of themselves for continued research or clinical use.

In another alternate embodiment, the GMPs disclosed herein are derived from cord blood stem cells. Umbilical cord blood is the blood left over in the placenta and in the umbilical cord after the birth of the baby. The cord blood is composed of all the elements found in whole blood. It contains red blood cells, white blood cells, plasma, platelets and is also rich in hematopoietic stem cells. Hematopoietic stem cells can be isolated from cord blood using any number of isolation methods taught in the art, including those taught in Chularojmontri et al., J Med Assoc Thai 92 (3):S88-94 (2009). Moreover, commercial kits are available for isolation CD34+ cells (i.e., hematopoietic stem cells) from human umbilical cord blood from multiple vendors, including STEMCELL Technologies, Thermo Fisher Scientific, ZenBio, etc.

In yet another alternate embodiment, the GMPs disclosed herein are derived from non-embryonic stem cells. The non-embryonic stem cell can renew itself and can differentiate to yield some or all of the major specialized cell types of the tissue or organ. The primary roles of non-embryonic stem cells in a living organism are to maintain and repair the tissue in which they are found. Scientists also use the term somatic stem cell instead of non-embryonic stem cell, where somatic refers to cells of the body (not the germ cells, sperm or eggs). Non-embryonic stem cells have been identified in many organs and tissues, including brain, bone marrow, peripheral blood, blood vessels, skeletal muscle, skin, teeth, heart, gut, liver, ovarian epithelium, and testis. They are thought to reside in a specific area of each tissue (called a "stem cell niche"). In a living animal, non-embryonic stem cells are available to divide for a long period, when needed, and can give rise to mature cell types that have characteristic shapes and specialized structures and functions of a particular tissue.

In a particular embodiment, the GMPs disclosed herein are derived from hematopoietic stem cells (HSCs). HSCs can easily be isolated from umbilical cord blood and bone marrow. Such isolation protocols are known in the art and typically use CD34+ as a cell selection marker for the isolation of HSCs (e.g., see Lagasse et al., Nat Med. 6:1229-1234(2000)).

Stem cells are cells capable of differentiation into other cell types, including those having a particular, specialized function (e.g., tissue specific cells, parenchymal cells and progenitors thereof). Progenitor cells (i.e., "multipotent") are cells that can give rise to different terminally differentiated cell types, and cells that are capable of giving rise to various progenitor cells. Cells that give rise to some or many, but not all, of the cell types of an organism are often termed "pluripotent" stem cells, which are able to differentiate into any cell type in the body of a mature organism, although without reprogramming they are unable to dedifferentiate into the cells from which they were derived. As will be appreciated, "multipotent" stem/progenitor cells (e.g., granulocyte/macrophage progenitor cells (GMPs)) have a narrower differentiation potential than do pluripotent stem cells. Prior to derivation into GMPs, the stem cells disclosed herein can be genetically modified by use of any number of genetic engineering techniques, e.g., such as gene therapy, gene editing systems, homologous recombination, etc. Such modified stem cells may provide for enhanced therapies (e.g., see Nowakowski et al., Acta Neurobiol Exp (Wars) 73 (1):1-18 (2013)).

In the methods disclosed herein, the GMPs can be grown and expanded in a culture medium which includes a combination of factors and agents including, but not limited to, a growth factor (e.g., SCF), a B-Raf kinase inhibitor (e.g., GDC-0879), and a Wnt activator (e.g., SKL 2001) and/or a GSK-3 inhibitor (e.g., CHIR99021). The culture medium is a modified basal medium that is supplemented with various other biological agents. A basal medium refers to a solution of amino acids, vitamins, salts, and nutrients that is effective to support the growth of cells in culture, although normally these compounds will not support cell growth unless supplemented with additional compounds. The nutrients include a carbon source (e.g., a sugar such as glucose) that can be metabolized by the cells, as well as other compounds necessary for the cell's survival. These are compounds that the cells themselves cannot synthesize, due to the absence of one or more of the gene(s) that encode the protein(s) necessary to synthesize the compound (e.g., essential amino acids) or, with respect to compounds which the cells can synthesize, because of their particular developmental state the gene(s) encoding the necessary biosynthetic proteins are not being expressed as sufficient levels. A number of basal media are known in the art of mammalian cell culture, such as Dulbecco's Modified Eagle Media (DMEM), RPMI 1640, KnockOut™DMEM (KO-DMEM), and DMEM/F12, although any base medium that can be supplemented with agents which supports the growth of stem cells in a substantially undifferentiated state can be employed. It was further found herein, that a culture medium that comprises a ratio of one of the basal medias exemplified above (e.g., DMEM/F12) with a neural basal medium (or alternatively other basal medium such as IMDM and/or StemSpan™ SFEMII) unexpectedly provided for improved growth of the GMPs. In particular, a ratio of 5:1 to 1:5 of one of the basal medias exemplified above (e.g., DMEM/F12) to a neural basal medium can be used to culture the GMPs. In a further embodiment, the culture medium for growing GMPs comprises 1:1 of DMEM/F12 to a neural basal media.

As indicated above, the culture medium disclosed herein for growing GMPs may be supplemented with one or more additional agents, including, but not limited to insulin, transferrin, BSA fraction V, putrescine, sodium selenite, DL-α tocopherol, and linolenic acid. In a certain embodiment, the culture medium disclosed herein for growing GMPs is supplemented with insulin, transferrin, BSA fraction V, putrescine, sodium selenite, DL-α tocopherol, and linolenic acid.

As will be appreciated, it is desirable to replace spent culture medium with fresh culture medium either continually, or at periodic intervals, typically every 1 to 3 days. One advantage of using fresh medium is the ability to adjust conditions so that the cells expand more uniformly and rapidly than they do when cultured on feeder cells according to conventional techniques, or in conditioned medium.

Populations of GMPs can be obtained that are 4-, 10-, 20-50-, 100-, 1000-, or more fold expanded when compared to the previous starting cell population. Under suitable conditions, cells in the expanded population will be 50%, 70%, or more in the undifferentiated state, as compared to the GMPs used to initiate the culture. The degree of expansion per passage can be calculated by dividing the approximate number of cells harvested at the end of the culture by the approximate number of cells originally seeded into the culture. Where geometry of the growth environment is limiting or for other reasons, the cells may optionally be passaged into a similar growth environment for further expansion. The total expansion is the product of all the expansions in each of the passages. Of course, it is not necessary to retain all the expanded cells on each passage. For example, if the cells expand two-fold in each culture, but only about 50% of the cells are retained on each passage, then approximately the same number of cells will be carried forward. But after four cultures, the cells are said to have undergone an expansion of 16-fold. Cells may be stored by cryogenic freezing techniques known in the art.

As indicated in more detail herein, the GMPs can be grown and expanded in a culture medium which includes a combination of factors and agents including, but not limited to, a growth factor (e.g., SCF), a B-Raf kinase inhibitor (e.g., GDC-0879), and a Wnt activator (e.g., SKL 2001) and/or a GSK-3 inhibitor (e.g., CHIR99021).

A "growth factor" refers to a substance, e.g., a compound or molecule, that is effective to promote the growth of cells, e.g., stem cells, and which, unless added to the culture medium as a supplement, is not otherwise a component of the basal medium. Growth factors include, but are not limited to, stem cell factor (SCF), basic fibroblast growth factor (bFGF), acidic fibroblast growth factor (aFGF), epidermal growth factor (EGF), insulin-like growth factor-I (IGF-I), insulin-like growth factor-II (IGF-II), platelet-derived growth factor-AB (PDGF), and vascular endothelial cell growth factor (VEGF), activin-A, Wnt and bone morphogenic proteins (BMPs), insulin, cytokines, chemokines, morphogens, neutralizing antibodies, other proteins, and small molecules. Exogenous growth factors may also be added to a medium according to the disclosure to assist in the maintenance of cultures of GMPs in a substantially undifferentiated state. Such factors and their effective concentrations can be identified as described elsewhere herein or using techniques known to those of skill in the art of culturing cells. In a particular embodiment, the GMPs are cultured in a culture medium which comprises SCF.

A "B-Raf" kinase inhibitor refers to a substance, e.g., a compound or molecule, that blocks or reduces an activity of a protein called B-Raf kinase, or reduces an amount of B-Raf kinase. B-Raf is a kinase enzyme that helps control cell growth and signaling. It may be found in a mutated (changed) form in some types of cancer, including melanoma and colorectal cancer. Some B-Raf kinase inhibitors are used to treat cancer. Examples of B-Raf kinase inhibitor includes, but are not limited to, GDC-0879, PLX4032, GSK2118436, BMS-908662, LGX818, PLX3603, RAF265, RO5185426, vemurafenib, PLX8394, and SB590885. In a particular embodiment, a method disclosed herein comprises use of the B-Raf kinase inhibitor GDC-0879.

"Granulocyte colony-stimulating factor" or "GCSF" (also known as colony-stimulating factor 3 (CSF 3)), is a glycoprotein that stimulates the bone marrow to produce granulocytes and stem cells. The gene sequence, protein sequence and orthologs across various species are known in the art (see, e.g., NCBI Reference Sequence: NP 000750.1, which is incorporated herein by reference).

"Macrophage colony-stimulating factor" or "MCSF" (also known as colony-stimulating factor 1 (CSF 1)), is involved in the proliferation, differentiation, and survival of monocytes, macrophages, and bone marrow progenitor cells. The gene sequence, protein sequence and orthologs across various species are known in the art (see, e.g., NCBI Reference Sequence: NP_000748.4, which is incorporated herein by reference).

"Stem Cell Factor" or "SCF" (also known as KIT-ligand, KL, or steel factor) is a cytokine that binds to the c-KIT receptor (CD117). SCF can exist both as a transmembrane protein and a soluble protein. This cytokine plays an important role in hematopoiesis (formation of blood cells), spermatogenesis, and melanogenesis. The gene sequence, protein sequence and orthologs across various species are known in the art (see, e.g., NCBI Reference Sequence NP_000890.1, which is incorporated herein by reference).

A "Wnt activator" refers to compound or molecule that induces Wnt signaling pathways. The Wnt signaling pathways are a group of signal transduction pathways which begin with proteins that pass signals into a cell through cell surface receptors. Three Wnt signaling pathways have been characterized: the canonical Wnt pathway, the noncanonical planar cell polarity pathway, and the noncanonical Wnt/calcium pathway. All three pathways are activated by the binding of a Wnt-protein ligand to a Frizzled family receptor, which passes the biological signal to the Dishevelled protein inside the cell. Wnt comprises a diverse family of secreted lipid-modified signaling glycoproteins that are 350-400 amino acids in length. The type of lipid modification that occurs on these proteins is palmitoylation of cysteines in a conserved pattern of 23-24 cysteine residues. Palmitoylation is necessary because it initiates targeting of the Wnt protein to the plasma membrane for secretion and it allows the Wnt protein to bind its receptor due to the covalent attachment of fatty acids. Wnt proteins also undergo glycosylation, which attaches a carbohydrate in order to ensure proper secretion. In Wnt signaling, these proteins act as ligands to activate the different Wnt pathways via paracrine and autocrine routes. These proteins are highly conserved across species. They can be found in mice, humans, *Xenopus*, zebrafish, *Drosophila* and many others. Examples of Wnt activators includes, but are not limited to, SKL 2001, BML-284, WAY 262611, CAS 853220-52-7, and QS11. In a particular embodiment, a method disclosed herein comprises use of the Wnt activator SKL 2001.

A "GSK-3 inhibitor" as used herein refers to a compound or small molecule that inhibits the action of glycogen synthase kinase 3. Glycogen synthase kinase 3 is a serine/threonine protein kinase that mediates the addition of phosphate molecules onto serine and threonine amino acid residues. In mammals GSK-3 is encoded by two known genes, GSK-3 alpha (GSK3A) and GSK-3 beta (GSK3B). GSK-3 has recently been the subject of much research because it has been implicated in a number of diseases, including Type II diabetes (Diabetes mellitus type 2), Alzheimer's Disease, inflammation, cancer, and bipolar disorder. GSK-3 is active in a number of central intracellular signaling pathways, including cellular proliferation, migration, glucose regulation, and apoptosis. GSK-3 has also been shown to regulate immune and migratory processes. GSK-3 participates in a number of signaling pathways in the innate immune response, including pro-inflammatory cytokine and interleukin production. GSK-3 is also integrally tied to pathways of cell proliferation and apoptosis. GSK-3 has been shown to phosphorylate Beta-catenin, thus targeting it for degradation. Examples of GSK-3 inhibitors includes, but are not limited to, CHIR99021, CHIR98014, SB216763, BIO, A1070722, and AR-A014418. In a particular embodiment, a method disclosed herein comprises use of the GSK inhibitor CHIR99021.

The disclosure further provides methods to genetically modify the GMPs disclosed herein using genetic engineering techniques. In particular it was shown herein that the GMPs of the disclosure are susceptible to genetic modification techniques, thereby allowing for the use of the GMPs in basic scientific research and clinical therapeutic applications. Thus, expanded and genetically modified GMPs can be readily translated into broad clinical applications.

Accordingly, the disclosure further provides methods to genetically modify GMPs disclosed herein. Such methods, can include the step of genetically engineering modifications into GMPs by using a gene editing system, homologous recombination, or site directed mutagenesis. Particular examples of gene editing systems include TALEN and CRISPR.

In a certain embodiment, the CRISPR system is a type II CRISPR system and the Cas enzyme is Cas9, which catalyzes DNA cleavage. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defence in bacteria and archaea, Mole Cell 2010, January 15; 37(1): 7.

The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to target sequences comprising the protospacer and the corresponding PAM via heteroduplex formation between the spacer region of the crRNA and the protospacer DNA. Finally, Cas9 mediates cleavage of target sequence of PAM to create a DSB within the protospacer. In a certain embodiment, the RNA polymerase Ill-based U6 promoter is to drive the expression of tracrRNA.

Typically, in the context of an endogenous CRISPR system, formation of a CRISPR complex (comprising a guide sequence hybridized to a target sequence and complexed with one or more Cas proteins) results in cleavage of one or both strands in or near (e.g., within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence. In some embodiments, one or more vectors driving expression of one or more elements of a CRISPR system are introduced into a host cell (e.g., a GMP or stem cell) such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g., each in a different intron, two or more in at least one intron, or all in a single intron). In some embodiments, the CRISPR enzyme, guide sequence, tracr mate sequence, and tracr sequence are operably linked to and expressed from the same promoter.

In some embodiments, a CRISPR expression vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell (e.g., a GMP or stem cell). In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell.

In some embodiments, a vector comprises a regulatory element operably linked to an enzyme-coding sequence encoding a CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is less than about 25%, 10%, 5%, 1%, 0.1%, 0.01%, or lower with respect to its non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools. In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also indicated.

Indicated orthologs are also described herein. A Cas enzyme may be identified Cas9 as this can refer to the general class of enzymes that share homology to the biggest nuclease with multiple nuclease domains from the type II CRISPR system. Most preferably, the Cas9 enzyme is from, or is derived from, spCas9 or saCas9. By derived, it is meant that the derived enzyme is largely based, in the sense of having a high degree of sequence homology with, a wildtype enzyme, but that it has been mutated (modified) in some way as described herein.

It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this disclosure includes many more Cas9s from other species of microbes, such as SpCas9, SaCa9, St1Cas9 and so forth.

The gene editing systems (e.g., CRISPR and TALEN) can be used to genetically engineer modifications into the GMP or stem cells, such as replacing or disrupting an existing gene found in the GMP or stem cell (knockout). As shown in the Examples presented herein, the GMPs of the disclosure are particular susceptible to knockout mutations. Moreover, it is expected that additional knockouts could be easily created from the GMPs of the disclosure such as SIRPα gene knockouts and/or a PI3Kγ gene knockouts. Alternatively, the same editing systems (e.g., CRISPR and TALEN) can be used to alter a genetic locus to contain sequence information not found at the genetic locus (a knock-in mutation). Such modifications, can be used to create GMP's that have "gained a function." Such modified GMPs are particular useful for mimicking a disease state, e.g., by expressing biomolecules associated with a disease or disorder.

The disclosure further provides for the differentiation of the GMPs into myeloid and lymphoid lineages of blood cells, such as monocytes, macrophages, granulocytes, neutrophils, basophils, eosinophils, erythrocytes, megakaryocytes to platelets, T cells, B cells, and natural killer cells. In a particular embodiment, a method disclosed herein further comprises differentiating the GMPs of the disclosure into macrophages by culturing the GMPs with a macrophage differentiation medium comprising MCSF. In yet a further embodiment, the macrophage differentiation medium comprises RPMI 1640, 10% FBS and 20 ng/mL of MCSF. In an alternate embodiment, a method disclosed herein further comprises differentiating the GMPs of the disclosure into granulocytes comprising: culturing the GMPs with a granulocyte differentiation medium comprising GCSF. In yet a further embodiment, the granulocyte differentiation medium comprises RPMI 1640, 10% FBS and 20 ng/mL of GCSF.

The following examples are intended to illustrate but not limit the disclosure. While they are typical of those that might be used, other procedures known to those skilled in the art may alternatively be used.

EXAMPLES

Figure 1B:
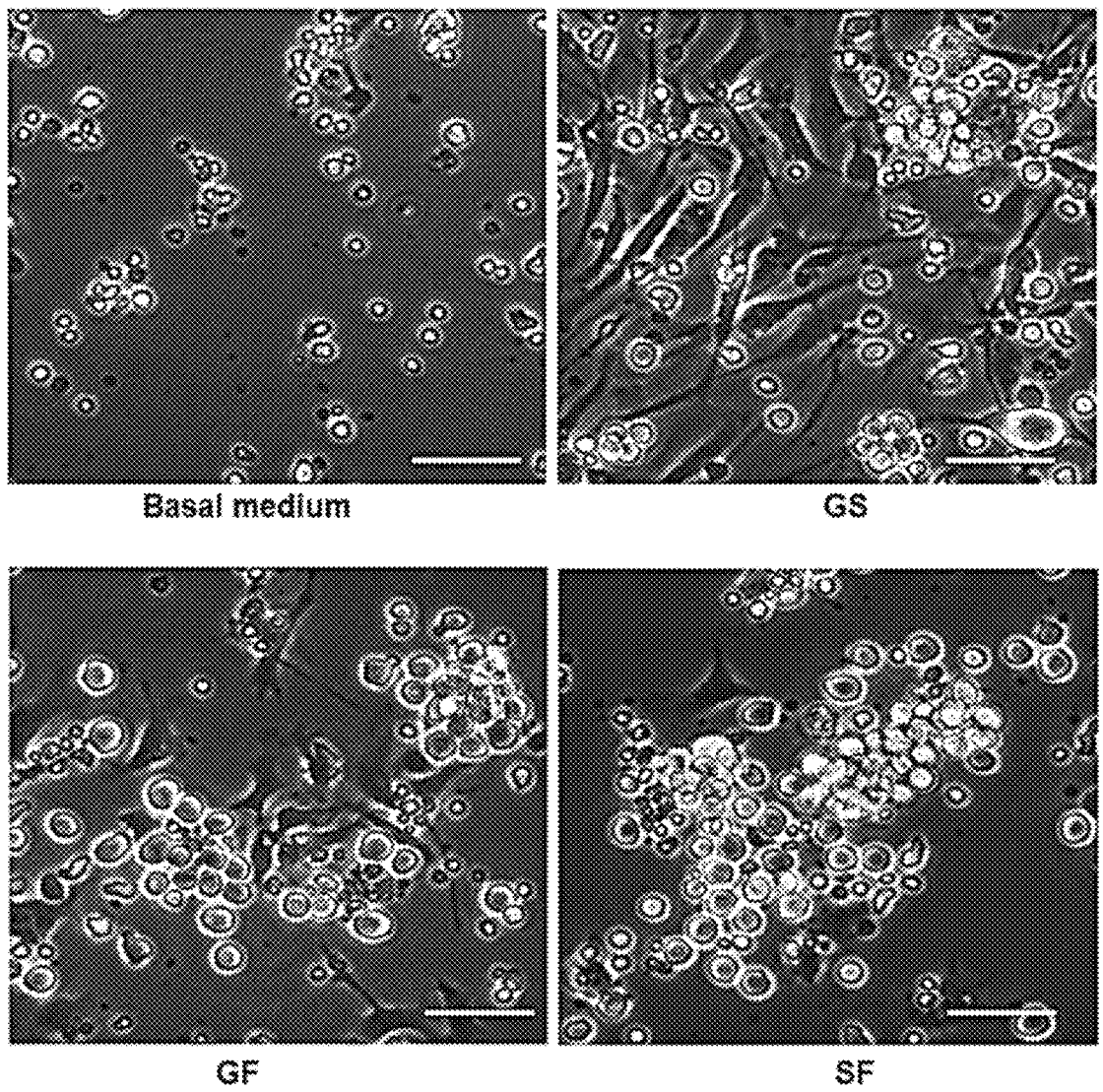
Figure 1C:
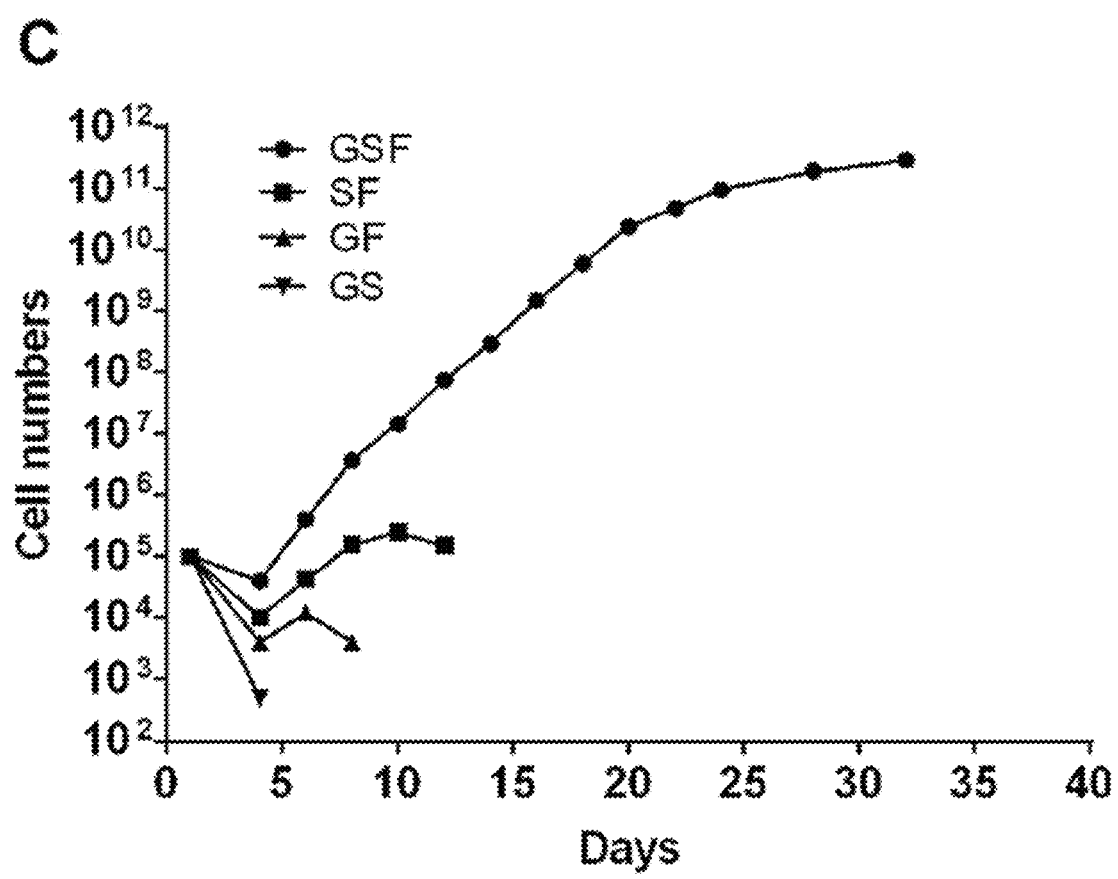

Determining whether the particular combination of SCF, GDC and SKL is important for long term mouse and human GMP cell expansion. To determine whether SCF, GDC, and SKL are all important for the long-term expansion of mouse GMPs, mouse GMPs were cultured in the absence of SCF, GDC, or SKL. As shown in FIG. 1B, after 3 days, almost all cells died in the basal medium only group, and most cells differentiated and attached to the plate without SCF. Although GMPs cultured in (SCF+GDC) or (SCF+SKL) could be passaged 3 to 5 times, they eventually differentiated and died. In contrast, GMPs cultured in SCF/2i could be propagated for long-term (e.g., see FIGS. 1B and 1C). Mouse GMPs had been continuously expanded in SCF/2i for more than 2 months remained morphologically unchanged.

Next, it was tested whether the SCF/2i condition also allows the expansion of human GMPs. CD34$^+$ cells were isolated from human umbilical cord blood using the EasySep™ human cord blood CD34 positive selection kit (STEMCELL Technologies Inc. Vancouver, Canada) and cultured in N2B27 medium supplemented with SCF/2i. Uniform bright, small and round-shaped cells similar to mouse GMPs emerged after 3-5 days in culture. These human cells could be expanded for several passages but gradually died or differentiated as passage number increased and could not be propagated beyond passage numbers 8-10. SKL was replaced with a GSK3 inhibitor (CHIR99021) and it was found that the combination of SCF, GDC, and CHIR allowed for the long-term expansion of human GMPs derived from umbilical cord blood, bone marrow, and G-CSF-mobilized CD34 peripheral blood stem cells. It was further found that some components in the B27 supplement adversely affected expansion of both mouse and human GMPs. After experimentation, a simplified version of the basal medium was developed that further improved the expansion of both mouse and human GMPs. This simplified basal medium comprises DMEM/F12 and Neural Basal Medium (mixed in 1:1 ratio) that was supplemented with insulin, transferrin, BSA fraction V, putrescine, sodium selenite, DL-α tocopherol, and Linolenic acid. The foregoing simplified basal medium has been termed E7 medium in the disclosure.

Figure 2A:
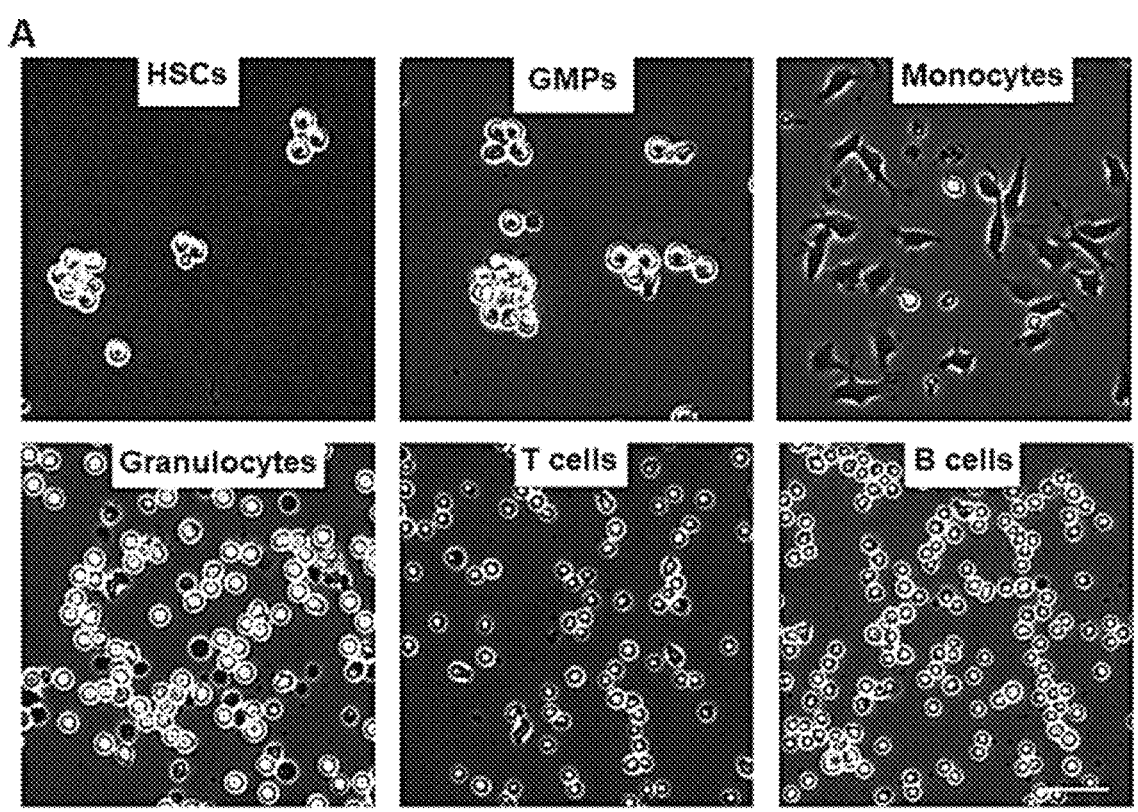
FIG. 2A-B provides for the characterization of GMP cells derived from mouse bone marrow cells that were cultured in SCF/2i medium. (A) Images of HSCs (Lin$^-$ cKit$^+$ Sca1$^+$ Flk2$^-$ CD34$^-$ Slam$^+$), GMPs (Lin$^-$ cKit$^+$ Sca1$^-$ FcgR$^+$), Monocytes (Mac1$^+$ CD115$^+$ B220$^-$ TCRab$^-$), Granulocyte (Mac1$^+$ CD115$^-$ Gr1$^+$ B220$^-$ TCRab$^-$), T cells (TCRab$^+$ Gr$^-$ Malc$^-$ B220$^-$) and B cells (B220$^+$ CD19$^+$ Gr1$^-$ Mac1$^-$ TCRab$^-$) were freshly isolated from bone marrow cells by using BD Arial flow cytometry. All cells were cultured in SCF/2i condition, representative pictures were taken 2 days after plating. Scale bar: 200 μm. (B) Presents flow cytometry data of cell surface markers. GMPs: Lin$^-$ cKit$^+$ Sca1$^-$ FcgR$^+$.
Figure 2B:
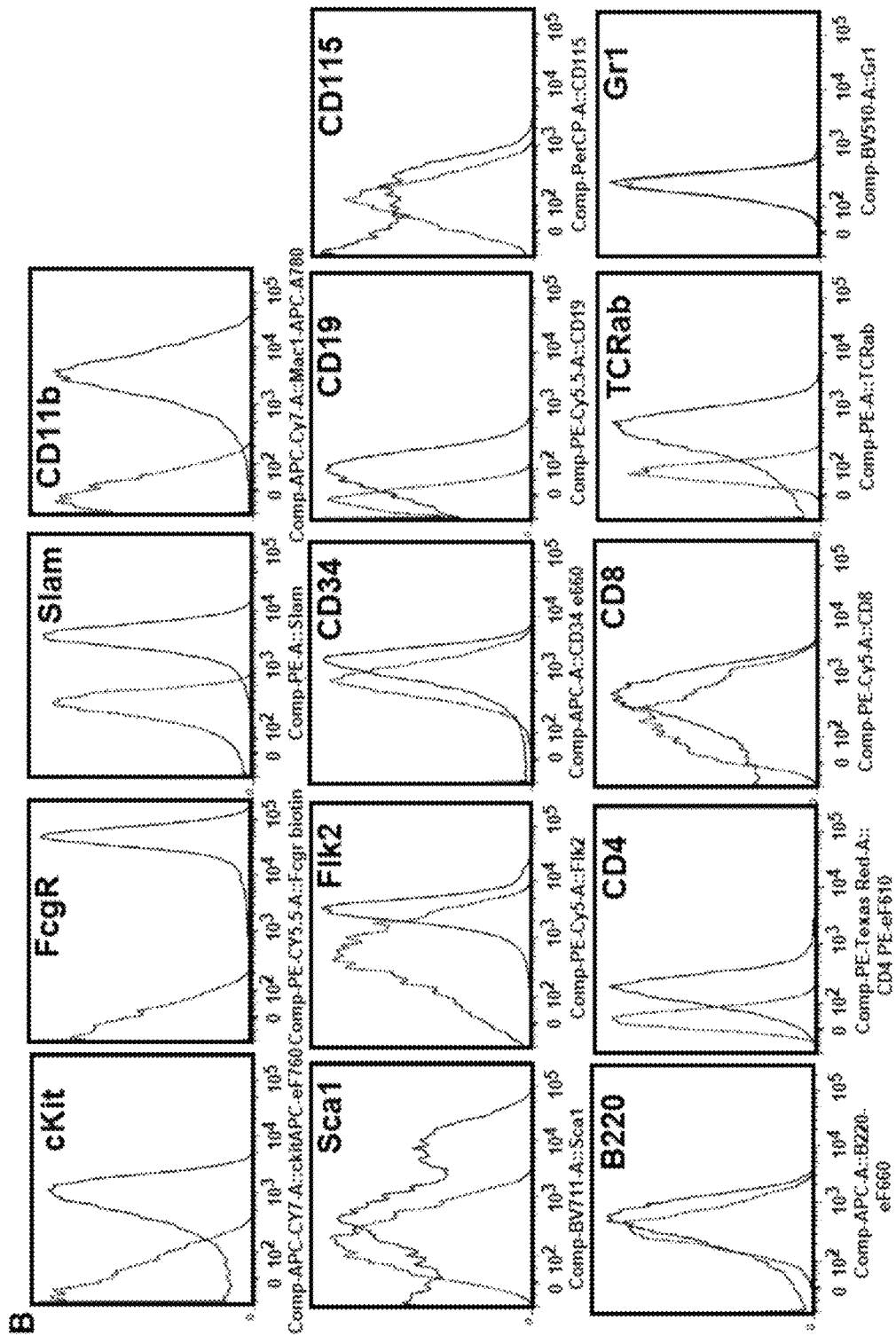

Characterization of mouse GMPs. To characterize the cultured GMPs, fresh bone marrow cells were first isolated and then a flow cytometer was used to sort out different hematopoietic stem/progenitor cells including hematopoietic stem cells (HSCs) (Lin–cKit$^+$ Sca1$^+$ Flk2$^-$ CD34$^-$ Slam$^+$), GMPs (Lin$^-$ cKit$^+$ Sca1$^-$ CD34$^+$ FcgR$^+$), monocytes (Mac1$^+$ CD115$^+$ B220$^-$ TCRab$^-$), granulocytes (Mac1$^+$ CD115$^-$ Gr1$^+$ B220$^-$ TCRab$^-$), T cells (TCRab$^+$ Gr$^-$Malc$^-$ B220$^-$) and B cells (B220$^+$ CD19$^+$ Gr1$^-$ Mac1$^-$ TCRab$^-$). These different types of cells were cultured with SCF/2i to determine which types of cells could be expanded and give rise to GMPs. It was found that HSCs and GMPs formed identical cell colonies and that these cells were able to self-renew for long-term expansion when SCF/2i was used. However, no colonies formed in other groups of cells (e.g., see FIG. 2A). These results indicated that the expanded cells using SCF/2i are likely a type of stem cells of the myeloid lineage. Next, after passage 3, the cells were harvested and the cell surface markers were checked by flow cytometer after staining. As shown in FIG. 2B, these cells were cKit$^+$ Sca1$^-$ CD34$^+$ FcgR$^+$, which indicates they are GMPs. GMPs can give rise to granulocytes, macrophages, and dendritic cells. Next, an in vitro differentiation assay was performed to further characterize these ex vivo expanded GMPs.

Figure 3A:
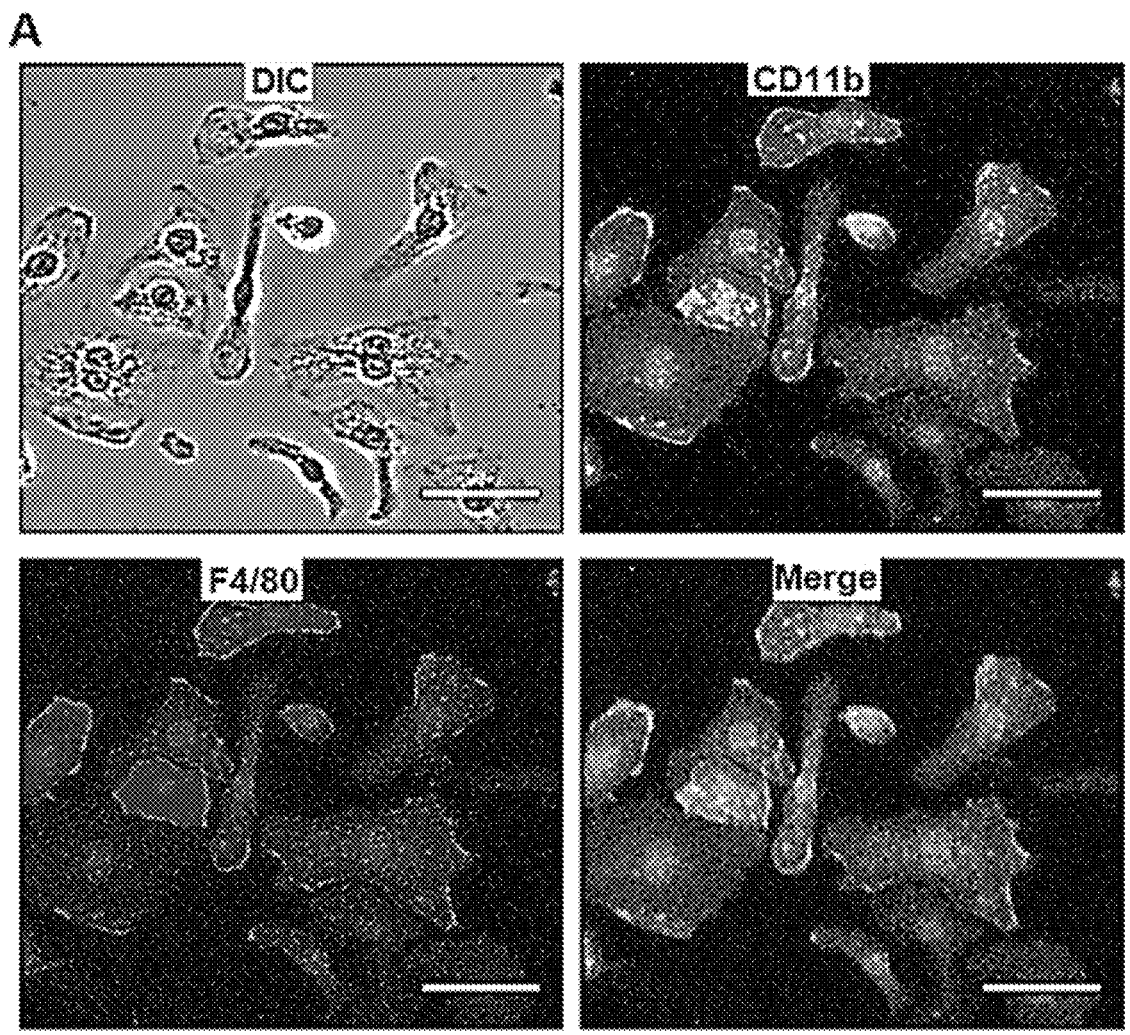
FIG. 3A-I presents results of macrophages differentiation from GMPs. (A) Presents images demonstrating macrophage differentiation. P7 GMPs were cultured in RPMI 1640+10% FBS+20 ng/mL MCSF for 7 days. Mature macrophages were re-plated, fixed and stained for CD11b and F4/80. (B) Provides the results of an in vitro functional test of the differentiated macrophages. $1×10^5$ GMPs (P7) or $1×10^6$ whole BM cells were seeded into 1 well of 6-well plate in RPMI 1640+10% FBS+20 ng/mL MCSF. 7 days later, mature bone marrow-derived macrophages (BMM) and GMP-derived macrophages (GMPM) were trypsinized, counted and reseeded into 48-well plate at $1×10^5$ cells per well in RPMI 1640+10% FBS. After overnight, cells were stimulated with 500 ng/mL LPS for 6 or 24 h. The inflammatory cytokines in the supernatant were measured by ELISA. (C) Provides images of another in vitro functional test of the differentiated macrophages. Green: *E. coli*-GFP. Red: tdTomato$^+$ macrophages. Top image, GFP labeled *E. coli* were co-cultured with tdTomato$^+$ GMPs-derived macrophages. Consecutive pictures were taken each 30' under Zeiss LSM-780 confocal microscope for 1 h. Scale Bar: 25 μm. Bottom, after washing off the uneaten bacteria, cells were fixed and stained for nuclear with DAPI, pictures were taken under Zeiss LSM-780 confocal microscope. (D-E) Provides images of a further in vitro functional test of the differentiated macrophages. FITC labeled latex beads were co-cultured with GMP-derived macrophages for 1 h. Green: FITC-beads. Blue: nuclear. (D), cells were fixed and stained with DAPI, pictures were taken under Zeiss microscope. (E), cells were harvested and FITC positive cells were analyzed by using BD Arial flow cytometry. (F-G) Presents the results of granulocytes differentiation. Basal medium: RPMI 1640+ 10% FBS. (H-I) Provides the results of an in vitro functional test using the differentiated granulocytes. (H) Results looking at MPO activity of the differentiated granulocytes; and (I) Results looking at cytokine expression/release of the differentiated granulocytes.
Figure 3B:
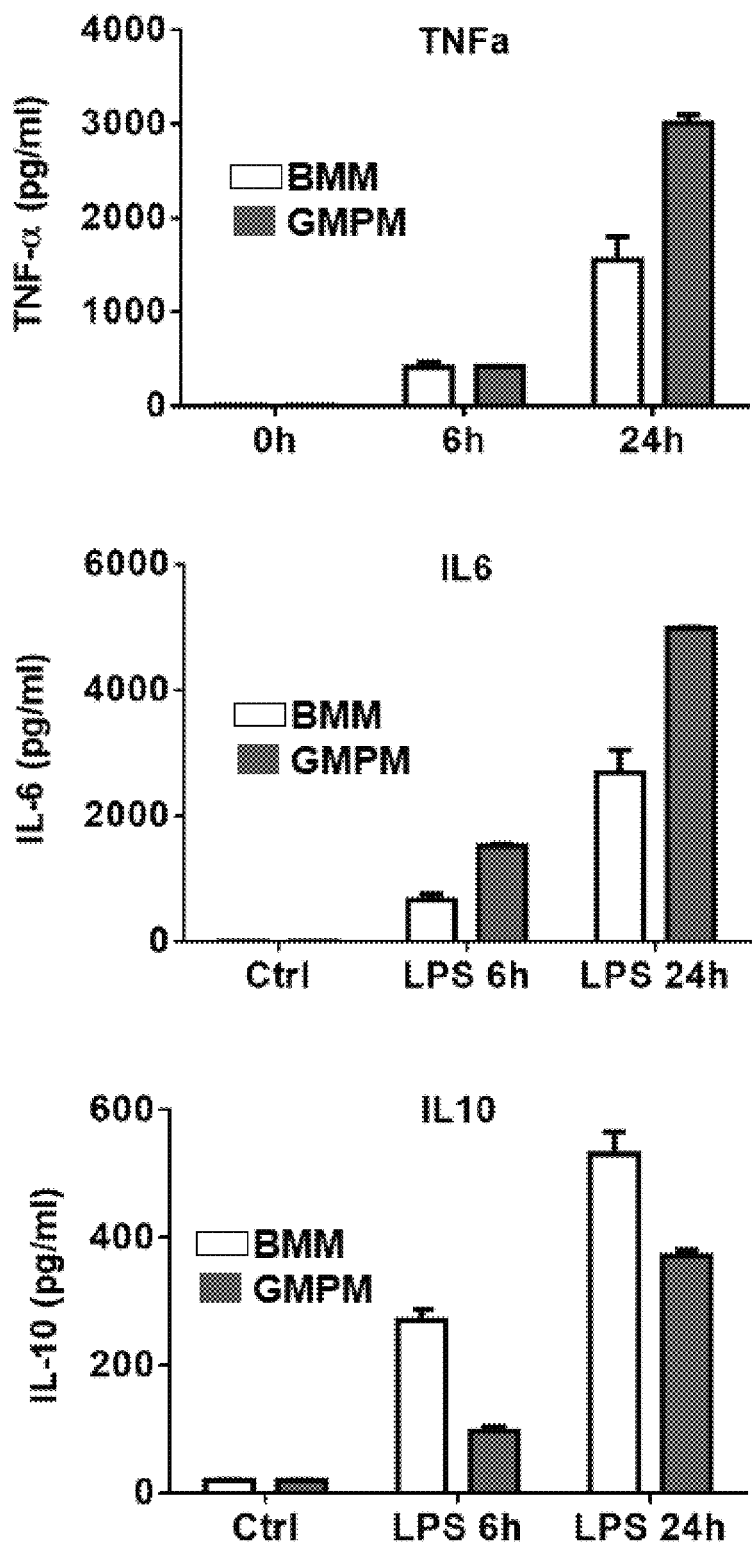

Long-term ex vivo expanded GMPs can differentiate into functional and mature macrophages. To induce differentiation into mature macrophages, 1×10$^5$ ex vivo expanded GMPs were plated per well into a 6-well plate and cultured in RPMI 1640+10% FBS+20 ng/mL MCSF. The cells proliferated, started to attach, and differentiate 3 days after plating. By day 7, the total cell number increased to ~2×10$^6$. The cells were passaged and re-plated at 1×10$^5$ cells per well in a 24-well plate. Twenty-four hours after plating, the cells were fixed and stained with the macrophage markers CD11b and F4/80, and DAPI for the nuclei. It was found that almost all the cells expressed both CD11b and F4/80 (e.g., see FIG. 3A), suggesting that GMPs have been induced to differentiate into macrophages. As one major type of the innate immune cells, macrophages perform their functions by phagocytosis and secreting inflammatory cytokines. It is well-known that macrophages express high level of toll-like receptor 4 (TLR4) and the activation of TLR4 by LPS dramatically increases the production of inflammatory cytokines. To test whether macrophages derived from GMPs can secrete inflammatory cytokines, GMP-derived macrophages (GMPMs) or bone marrow-derived macrophages (BMMs) were plated at 1×10$^5$ cells/well into 48-well plates and then stimulated with 500 ng/mL LPS. After 6 or 24 h, the supernatant was harvested and the concentrations of inflammatory cytokines TNFα, IL6 and IL10 by ELISA were measured. As expected, these cytokines were significantly increased after LPS stimulation. Interestingly, GMPMs secreted more pro-inflammatory cytokines TNFα and IL6 and less anti-inflammatory cytokine IL10, as compared to BMMs (e.g., FIG. 3B).

Figure 3C:
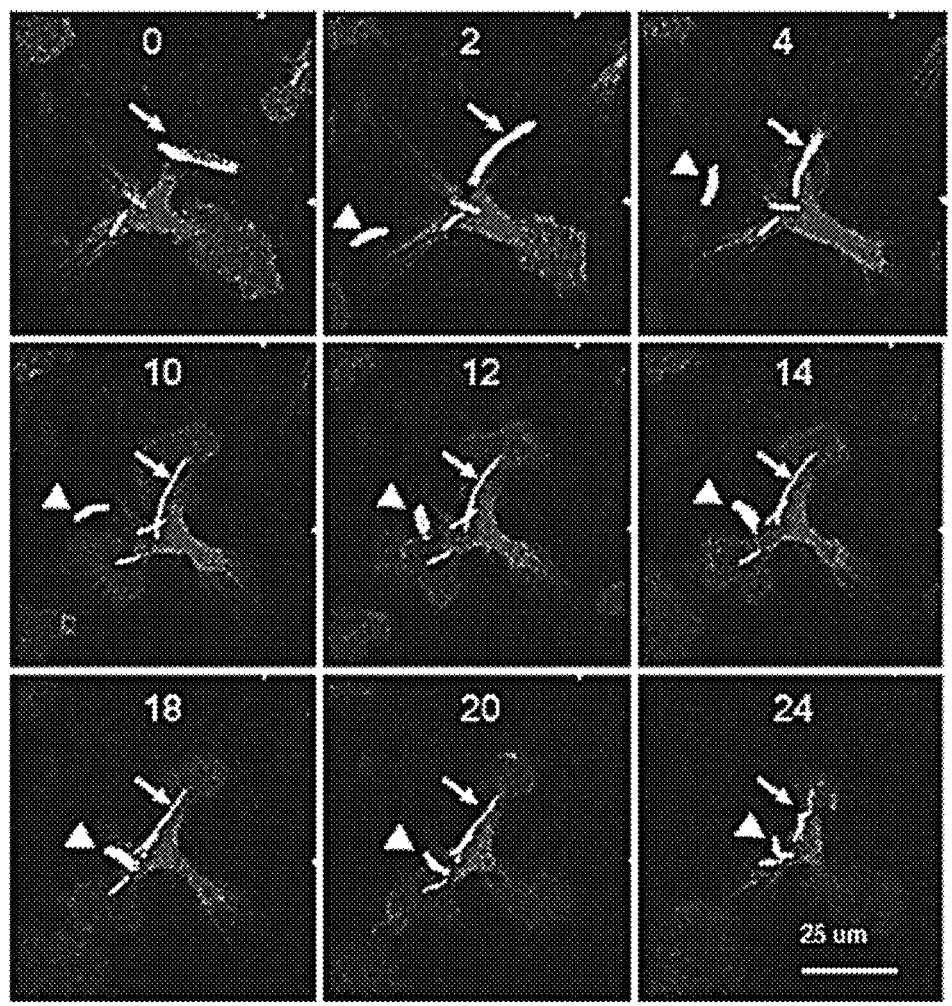
Figure 3C:
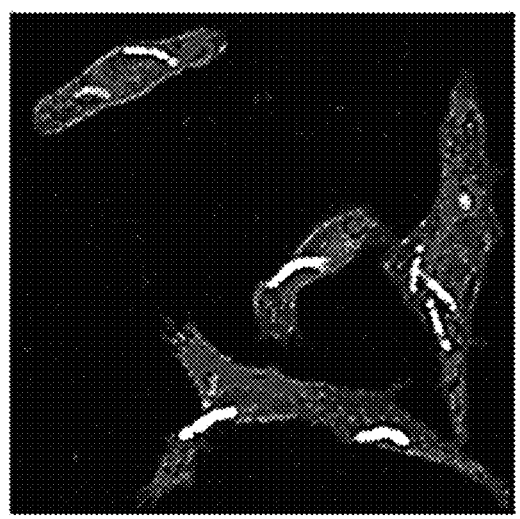
Figure 3D:
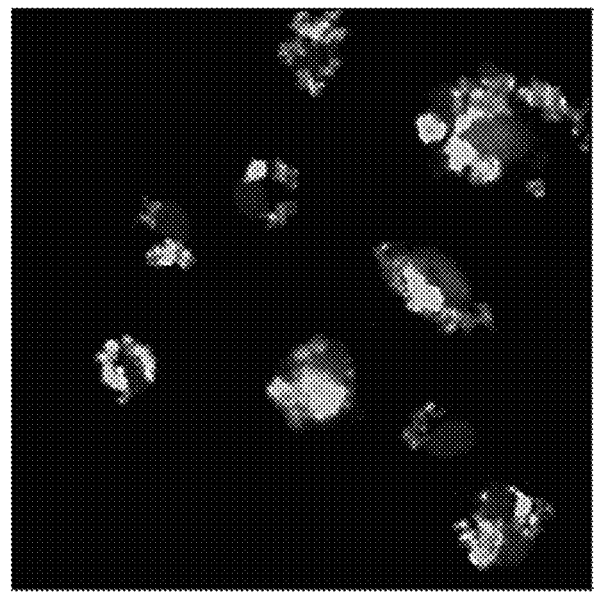
Figure 3E:
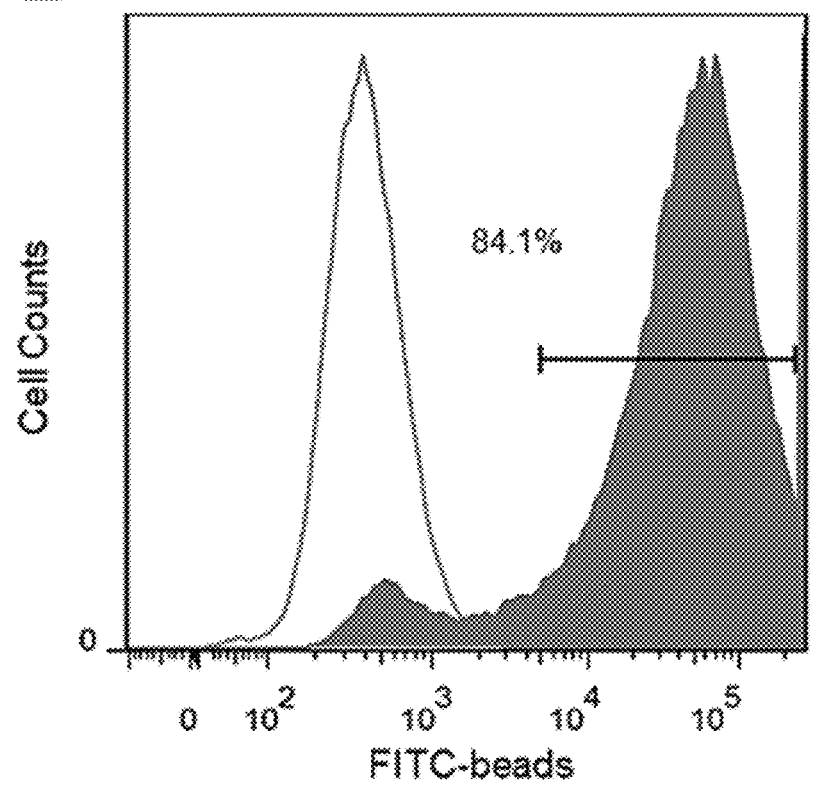

To evaluate GMPM's phagocytosis function, GMPs were derived from the Rosa26-CAG-tdTomato knockin mouse. In this mouse, the tdTomato fluorescent protein is expressed in all cells. After expansion using SCF/2i for 7 passages, tdTomato$^+$ GMPs were induced to differentiate into mature macrophages. These macrophages were then co-cultured with GFP-labeled E. coli. Time-lapse photography was then performed using a Zeiss LSM-780 confocal microscope for 1 h. It was found that GMPMs phagocytosed and digested bacteria very efficiently (e.g., see FIG. 3C). To further evaluate GMPM's phagocytotic efficiency, FITC-labeled latex beads were used to perform the phagocytosis assay using the manufacture's protocol. After co-culture with the latex beads for 30 minutes, GMPMs were either fixed and stained with DAPI or trypsinized and analyzed under flow cytometer. As shown in FIGS. 3D and 3E, more than 80% of macrophages phagocytosed the latex beads. Taken together, these results suggest that long-term ex vivo cultured GMPs are able to differentiate into mature and functional macrophages.

Figure 3F:
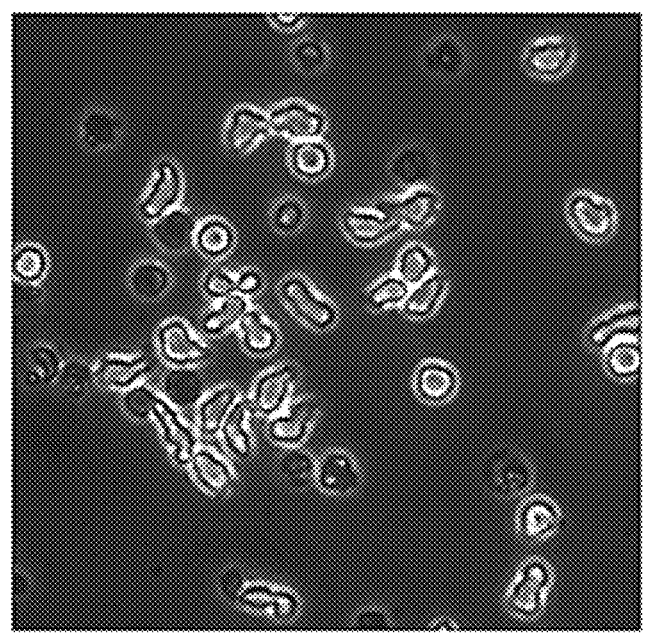
Figure 3G:
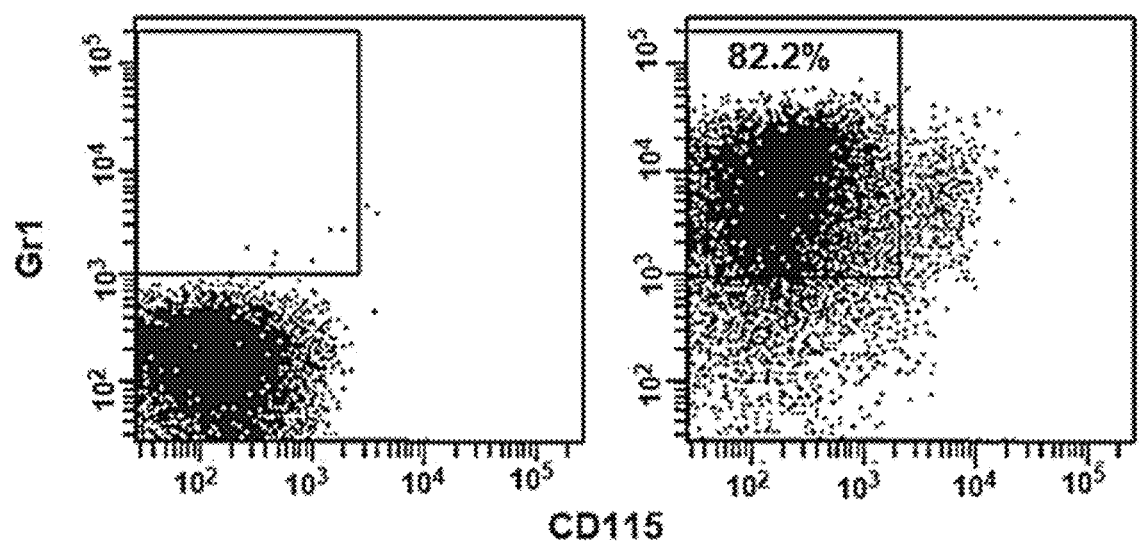

Long-term ex vivo expanded GMPs can differentiate into functional and mature granulocytes. Granulocyte colony-stimulating factor (G-CSF) is a known hematopoietic growth factor that regulates neutrophils production in the bone marrow. G-CSF was used to induce mouse GMP differentiation towards the neutrophil lineage. After culturing for 3 weeks in E7$^+$SCF/GDC/CHIR conditions, GMPs were re-plated in RPMI 1640+10% FBS medium and stimulated with 20 ng/mL of GCSF. Seventy-two hours after stimulation with GCSF, GMPs differentiated into cells that morphologically resembled granulocytes (e.g., see FIG. 3F). To further verify the identity of these cells, the cells were harvested and stained with Gr1 and CD115 antibodies and analyzed by flow cytometer. Granulocytes are Gr1$^+$ and CD115$^-$. As shown in FIG. 3G, more than 80% of the cells derived from GMPs were Gr1$^+$ CD115$^-$, suggesting that GMPs can be efficiently induced to differentiate into granulocytes by GCSF.

Figure 3H:
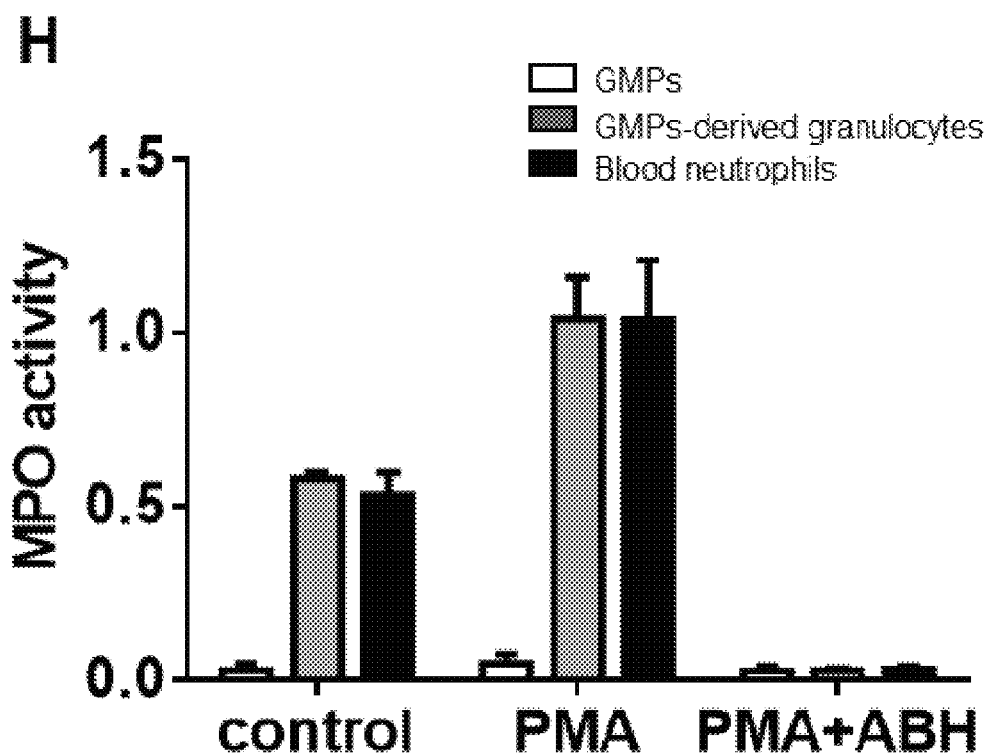

Myeloperoxidase (MPO) is released from granulocytes/neutrophils to degrade invading pathogens, providing one of the earliest lines of defense in innate immunity. To functionally evaluate mouse GMP-derived granulocytes, MPO activity was measured using an MPO activity assay kit (Cayman Chemical Company). Mouse neutrophils (Gr1$^+$ CD11b$^+$CD115$^-$) were sorted from the whole blood using BD Arial I flow cytometer and used as a positive control. GMPs, GMP-derived granulocytes and blood-originated neutrophils were plated into 96-well plates at 1×10$^5$ cells/well in RPMI 1640 medium containing 1% BSA. Cells were then stimulated with 100 nM phorbol myristate acetate (PMA) for 2 h and the MPO activities in the supernatants were measured following the manufactor's protocol. 4-aminobenzhydrazide (ABH), a specific inhibitor for MPO, was used to verify the specificity of the assay. As shown in FIG. 3H, MPO activity in undifferentiated GMPs couldn't be detected, while GMPs-derived granulocytes and blood neutrophils possessed similar MPO activities with PMA stimulation (1.039±0.122 vs 1.037±0.173, p=0.98) or without (0.580±0.017 vs 0.535±0.062, p=0.29) PMA stimulation. As expected, MPO activities in PMA-stimulated GMP-derived granulocytes and blood neutrophils were both blocked (e.g., see FIG. 3H).

Figure 3I:
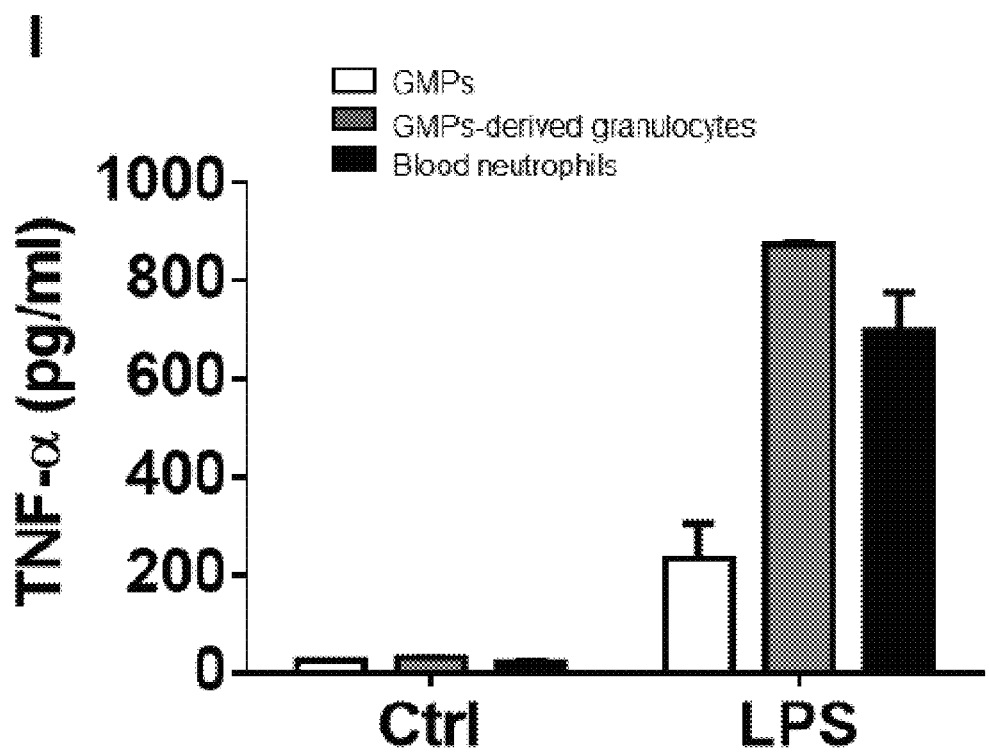
Figure 3I:
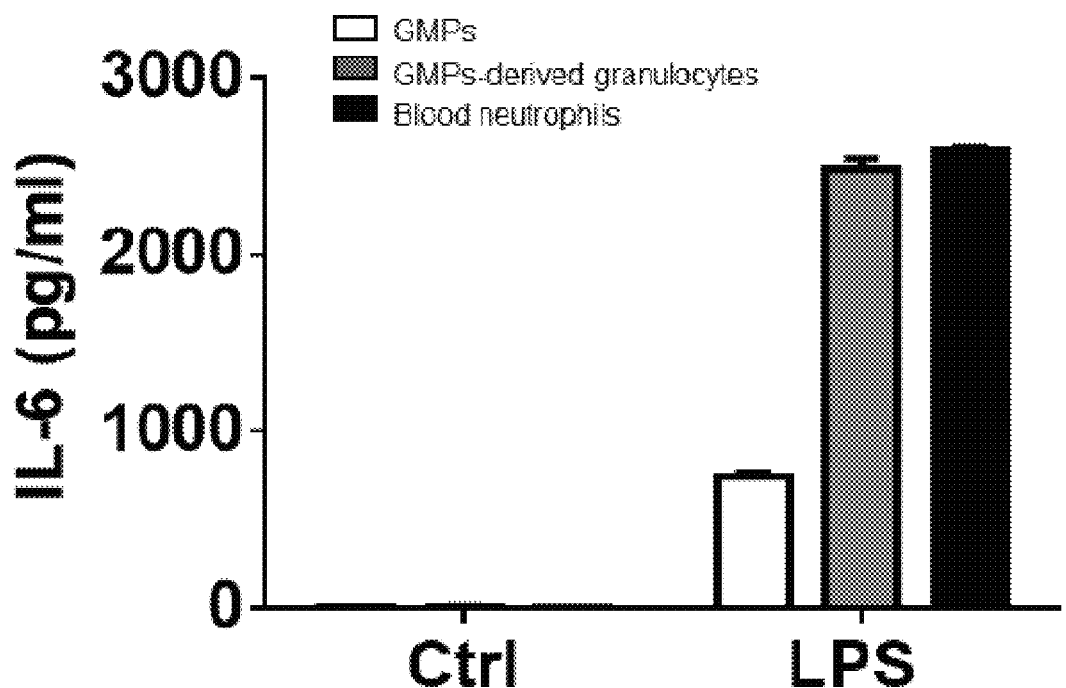
Figure 3I:
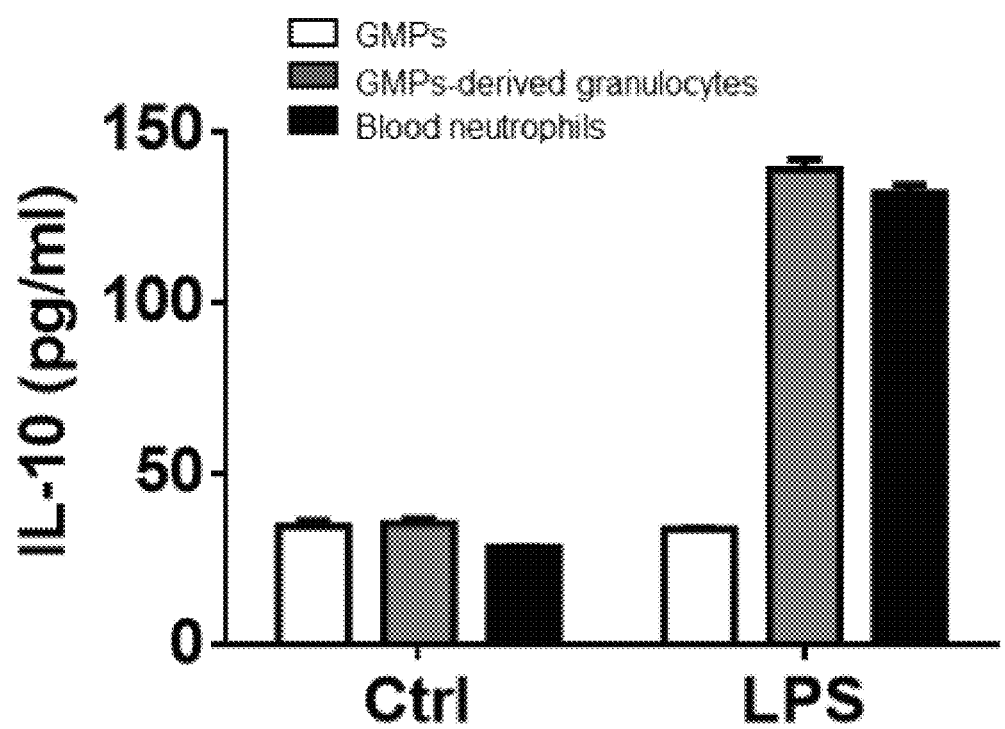

Since neutrophils also express high levels of TLR4, the GMPs-derived granulocytes were stimulated with LPS to further evaluate their cytokine generating abilities. GMPs, GMPs-derived granulocytes and blood neutrophils were plated at 1×10$^5$ cells/well into 96-well plates in RPMI 1640 medium containing 10% FBS. The cells were stimulated with 500 ng/mL LPS. Twenty-four hours later, the supernatants were collected and the inflammatory cytokines TNFα, IL6 and IL10 were measured by ELISA. The results showed that GMPs-derived granulocytes secreted similar amounts of inflammatory cytokines as compared to blood neutrophils upon LPS stimulation (e.g., see FIG. 3I), interestingly, undifferentiated GMPs also responded to LPS and secreted low levels of TNFα and IL6 (e.g., see FIG. 3I). Taken together, these results suggest that ex vivo expanded GMPs retain the ability to differentiate into mature and functional granulocytes.

Figure 4A:
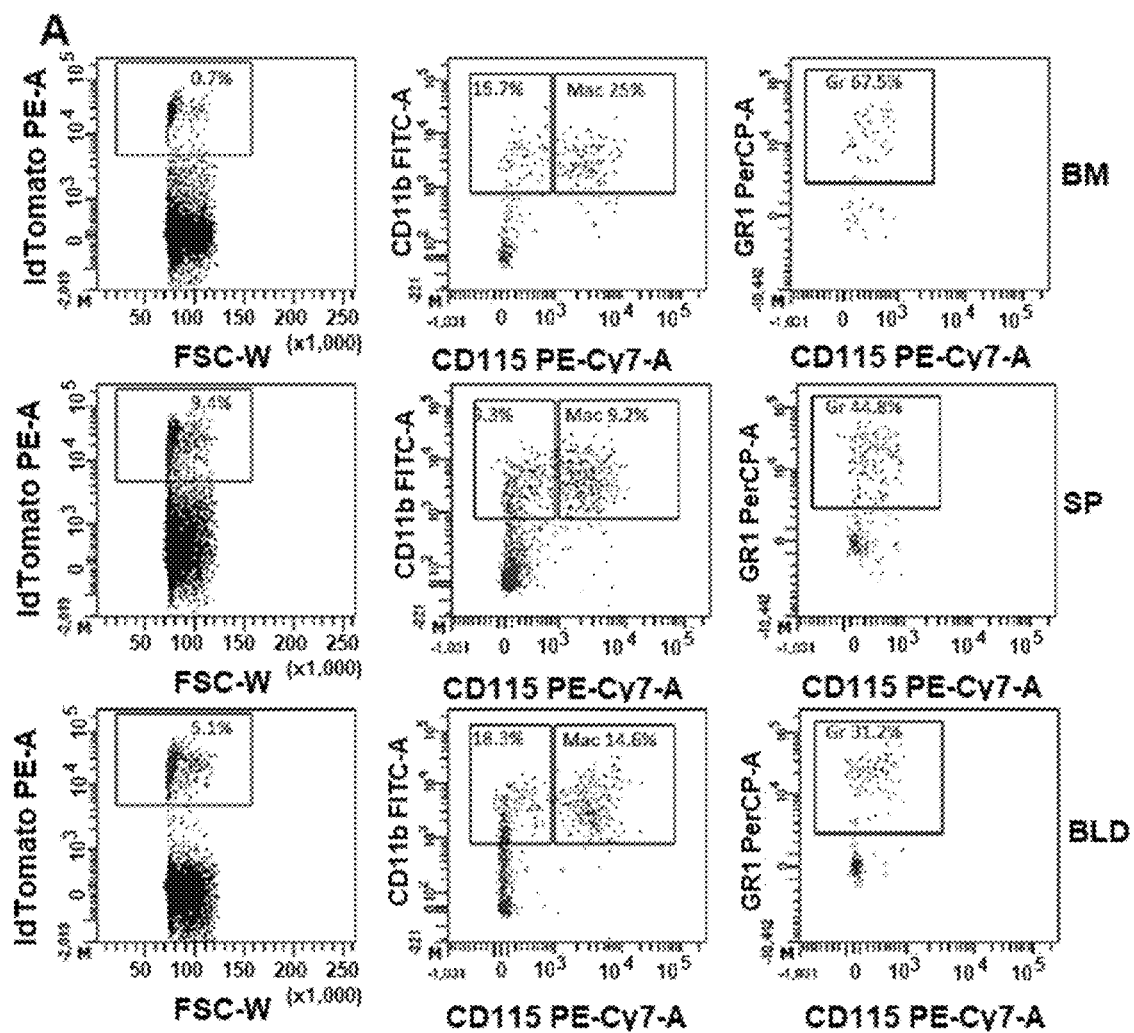
FIG. 4A-D demonstrates the results of in vivo mouse study where mice have been transplanted tdTomato$^+$ GMPs. (A) Day 1, FAC analysis. Mac: Macrophages, and Gr: granulocytes. (B) FACS analysis for macrophages and granulocytes differentiation at different time points. (C) Double immunostaining for macrophages and tdToamto positive cells of the livers from GMPs transplanted mice. $3×10^6$ tdTomato$^+$ GMPs were transplanted into each mouse via tail vein injection. 7 days later, mice were sacrificed and liver tissues were fixed, sliced and stained for F4/80 and tdTomato. (D) Peritoneal macrophages from mice which received GMPs transplantation. $3×10^6$ GMPs were injected via tail vein, and 1 mL Bio-Gel p100 was injected i.p., peritoneal macrophages were harvested and plated 4 days after transplantation.
Figure 4B:
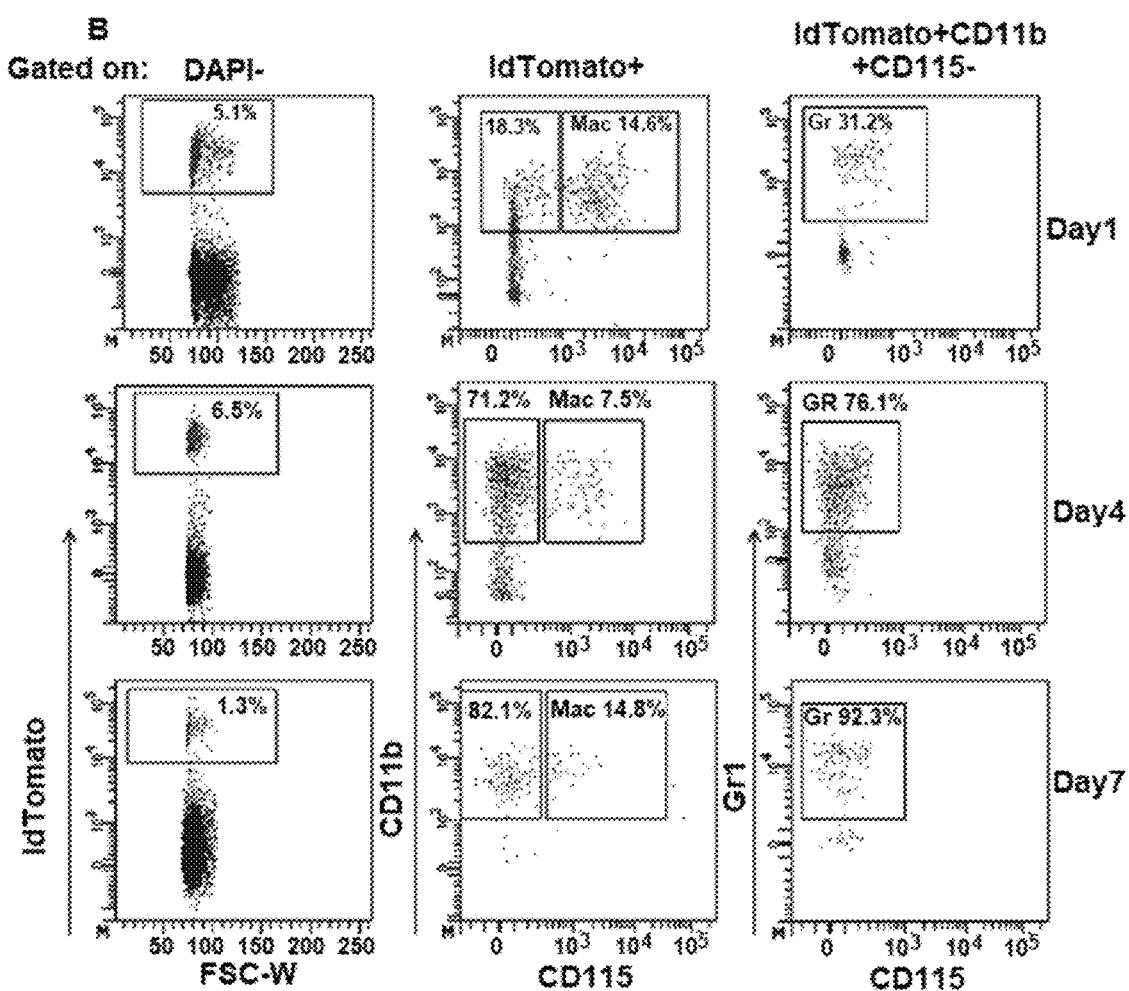
Figure 4C:
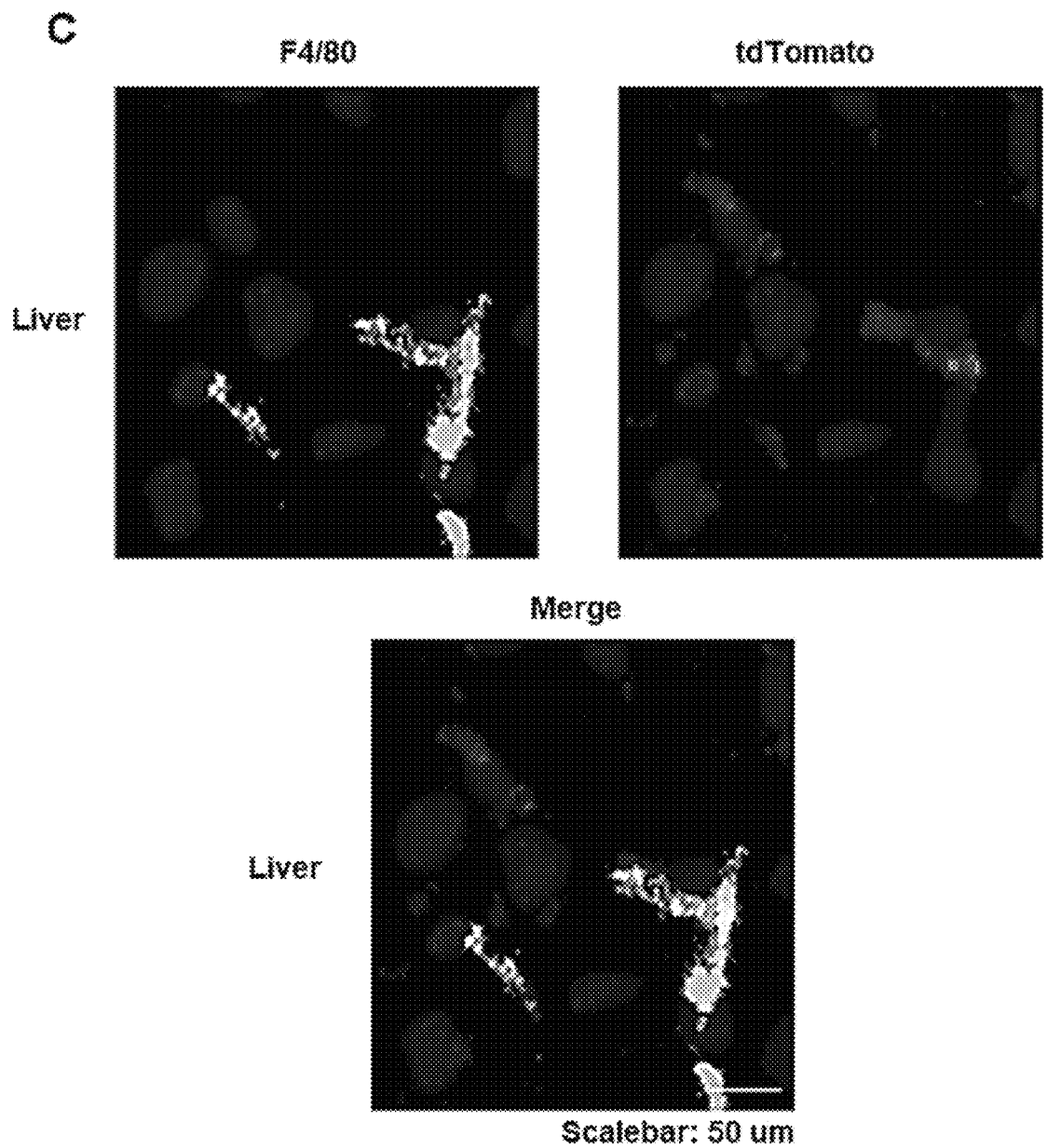
Figure 4D:
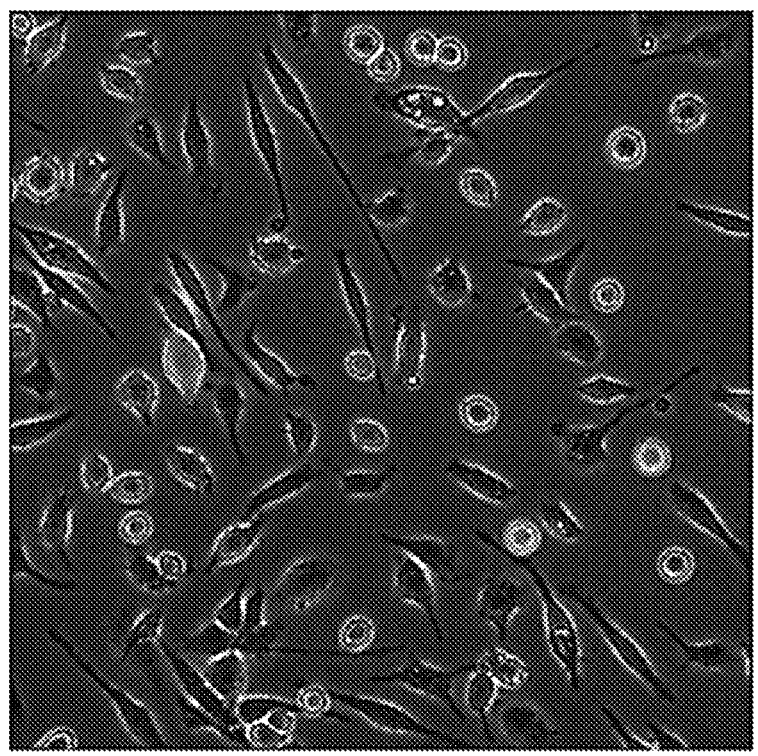

Long-term ex vivo expanded GMPs can differentiate into both granulocytes and macrophages in vivo. To determine the differentiation potential of the expanded GMPs in vivo, we expanded tdTomato+ mouse GMPs were expanded for 4 weeks with SCF/2i and then transplanted into C57BL/6 mice at $2 \times 10^6$ cells per mouse via tail vein injection. Mice were sacrificed at days 1, 4, 7 or 14 after transplantation. Blood, spleen and bone marrow cells were isolated, stained and analyzed by FACS. The liver tissues were harvested, sectioned and stained for Tdtomato and F4/80, a marker for macrophages. One day after transplantation, 0.7%, 9.4%, and 5.1% of the total bone marrow, spleen and white blood cells were positive for tdTomato, respectively. Among these tdTomato$^+$ cells, about 10-25% already differentiated into macrophages (CD115$^+$ CD11b$^+$) and 4-10% differentiated into neutrophils (CD115–CD11b$^+$ Gr1$^+$) (e.g., see FIG. 4A). The donor cells differentiated and decreased gradually in the blood, and the majority of them differentiated into mature macrophages (14.8%) and neutrophils (75.8%) 7 days after transplantation (e.g., see FIG. 4B). Mature donor-derived macrophages (tdTomato$^+$F4/80$^+$) could also be found in the livers (e.g., see FIG. 4C). It is well known that injection of Bio-Gel polyacrylamide beads or thioglycolate broth into the peritoneal cavity can produce an inflammatory response and trigger the accumulation of a large number of macrophages. To determine whether these GMPs-derived macrophages were also responsible to inflammatory stimuli, $3 \times 10^6$ tdTomato$^+$ GMPs were transplanted per mouse via tail vein and 2% Bio-Gel p-100 (1 mL) was i.p. injected at the same time. 4 days after injection, peritoneal macrophages were collected and cultured in RPMI 1640+10% FBS. About 1-2% of peritoneal macrophages were differentiated from the transplanted GMPs (e.g., see FIG. 4D). These results suggest that long-term ex vivo expanded GMPs are able to differentiate into mature macrophages and neutrophils and respond to inflammatory stimulation in vivo.

Transplantation of ex vivo expanded QHPs protectsx-linked CGD mice from bacterial infection. Chronic granulomatous disease (CGD) is a group of inherited disorders characterized by a defective phagocyte respiratory burst oxidase, life-threatening pyogenic infections and inflammatory granulomas. A mouse model of CGD was generated by knocking out an X-linked gene encoding gp91phox, which is broadly used to study this disease. S. aureus is a common cause of soft tissue or visceral abscesses in CGD patients, and B. cepacia is an opportunistic gram-negative pathogen that can produce serious infections in patients with CGD, including pneumonia and associated sepsis. It has been reported that clearance of bacteria from the peritoneal cavity was impaired in X-linked CGD mice.

Figure 5A:
FIG. 5A-E provides for the characterization of mouse organs from mice that were transplanted with PBS or tdTomato$^+$ GMPs, which were i.p. injected with $2×10^7$ *S. aureus*. (A) Photographs of the internal organs of *S. aureus* treated mice that were transplanted with PBS or tdTomato$^+$ GMPs. Pustules are indicated by arrows. (B) Photographs of livers isolated from *S. aureus* treated mice that were transplanted with PBS or tdTomato$^+$ GMPs. Pustules are indicated by arrows. (C) Photographs of spleens isolated from *S.* aureus treated mice that were transplanted with PBS or tdTomato+ GMPs. (D) Percent survival of *S. aureus* treated mice that were transplanted with PBS or tdTomato+ GMPs. (E) Percent survival of *B. cepacia* 200 treated mice that were transplanted with PBS or tdTomato+ GMPs.
Figure 5A:
Figure 5B:
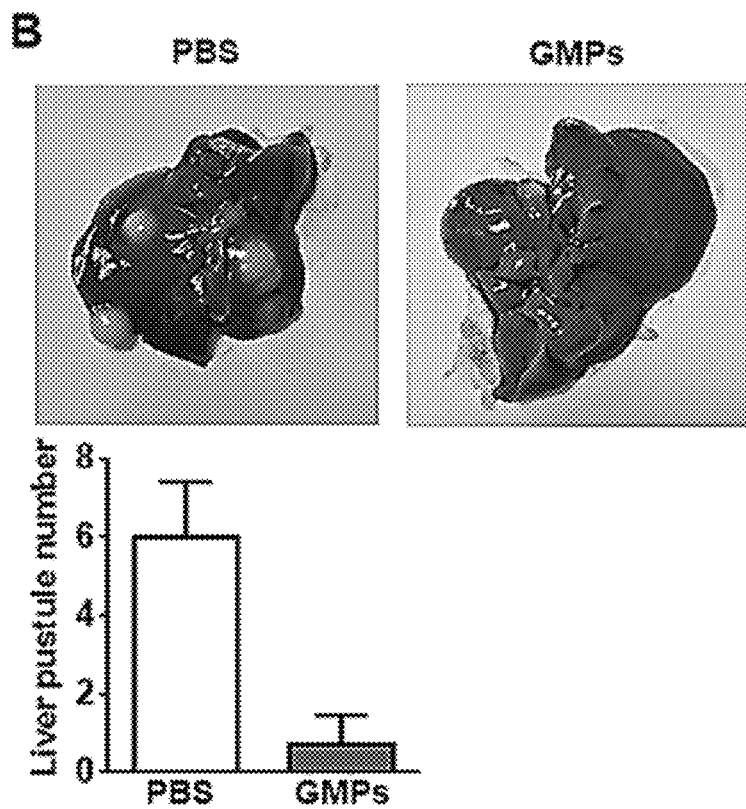
Figure 5C:
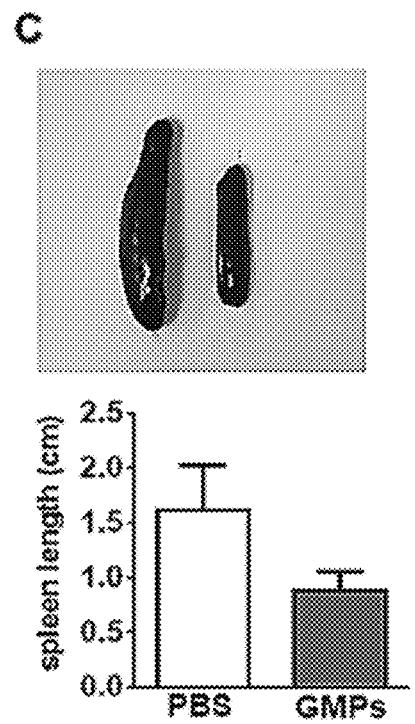
Figure 5D:
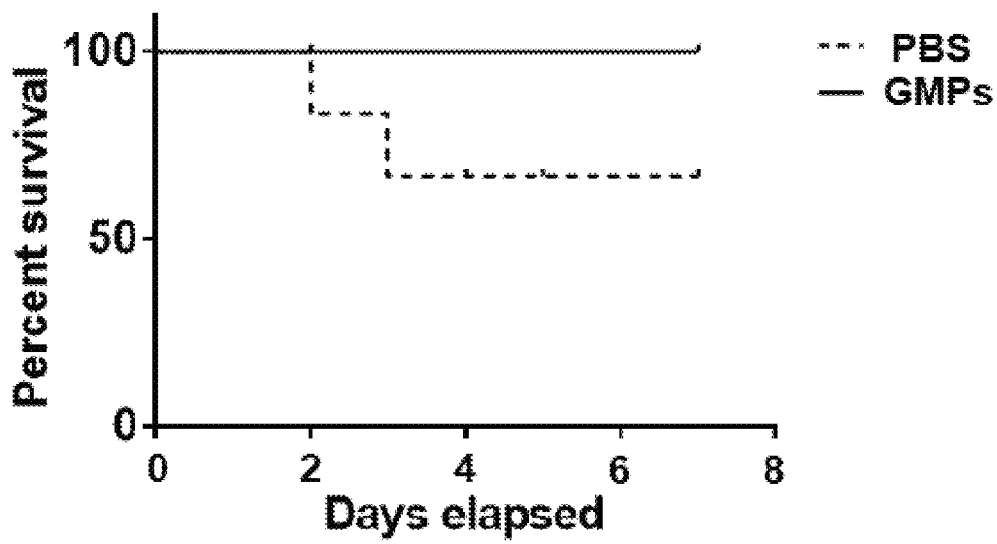
Figure 5E:
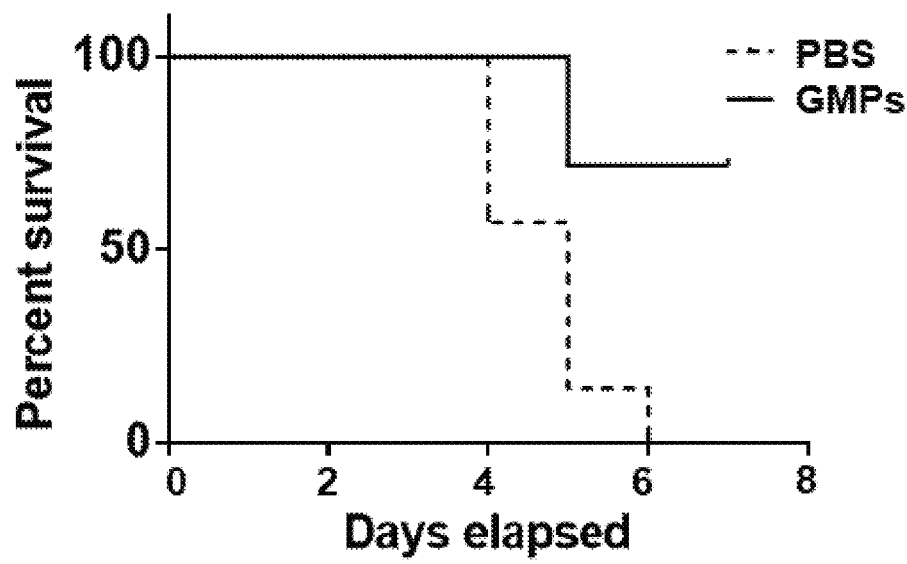

To further functionally characterize the ex vivo expanded GMPs, $3 \times 10^6$ GMPs were transplanted per mouse into gp91phox$^{-/-}$ mice via tail vein injection. In the control groups, the same volume of PBS was injected. Three days later, mice were injected intraperitoneally with a 0.2 ml suspension of $1 \times 10^8$/mL of S. aureus strain 502A (ATCC No. 27217; ATCC) or $1 \times 10^3$/mL of B. cepacia bacilli (ATCC No. 25609; ATCC). Mice were examined daily and sacrificed 2 weeks after peritoneal bacteria challenge. As shown in FIG. 5A, the control group mice developed severe infections after S. aureus challenge, and abscesses were found in several organs including the liver, spleen, gut and kidney. In direct contrast, abscesses were rare the group transplanted with GMPs. The livers were collected, and the numbers of abscesses were counted after the bacteria challenge. It was found that GMP transplantation significantly reduced the formation of abscesses as compared to the control group ($0.71 \pm 0.286$ vs $6.00 \pm 0.577$, $p<0.001$) (e.g., see FIG. 5B). It is known that active infection causes splenomegaly. Next, the size of spleens 2 weeks after S. aureus inoculation were measured. It was found that the spleens in the X-linked CGD mice were dramatically enlarged ($1.62 \pm 0.166$ cm) in the control group, whereas the sizes of the spleens of the GMP transplanted mice were similar to the normal size ($0.88 \pm 0.0.07$ cm) (e.g., see FIG. 5C). In addition, 2 of 8 mice died after S. aureus inoculation in the control group, while all 8 mice survived in the GMP transplanted group (e.g., see FIG. 5D). B. cepacia is an opportunistic gram-negative pathogen that can produce serious infections in patients with CGD, including pneumonia and associated sepsis. All the 10 control CGD mice injected with PBS and B. cepacia bacilli died in 6 days. In contrast, only 2 of the 10 mice injected with GMPs and B. cepacia bacilli died in 6 days (e.g., see FIG. 5E).

Genetic modification of ex vivo expanded GMPs. It is difficult to perform genetic modification in mature macrophages and granulocytes. Next, methods were developed for the efficient genetic modification in GMPs. A very highly efficient protocol to either overexpress or knockout a gene in GMPs was developed. As is shown in FIG. 6A, more than 95% of GMPs transfected with GFP mRNA were GFP positive. Next, genes were attempted to be knocked out by a CRISPR/Cas9 system. Guide RNAs were specifically designed and synthesized so as to target GFP or toll like receptor 4 (TLR4) genes. gRNAs targeting GFP were introduced into GMPs derived from the ROSA 26-CAG-Cas9-GFP mouse. About 91.1% of the GMPs transfected with GFP gRNAs became GFP negative 48 h after transfection (e.g., see FIG. 6B). A similar efficiency was achieved in knocking out the TLR4 gene in GMPs (e.g., see FIG. 6C). A GFP-GMP knockout and a TLR4-GMP knockout were differentiated into mature macrophages and stimulated with Poly I:C and LPS. Twenty-four hours later, the supernatant was harvested the amounts of inflammatory cytokines secreted by the cells was measured by ELISA. As shown in FIG. 6C, the concentrations of TNFα, IL-6 and IL-10 dramatically decreased in TLR4 knockout cells as compared to those in GFP knockout cells. As expected, the concentrations of the cytokines were similar in both groups of cells after stimulation with TLR3 ligand Poly I:C.

It will be understood that various modifications may be made without departing from the spirit and scope of this disclosure. Accordingly, other embodiments are within the scope of the following claims.

What is claimed is:

1. A method for the expansion of a population of granulocyte/macrophage progenitor cells (GMPs), comprising:
   culturing GMPs in a culture medium comprising:
   (i) a growth factor,
   (ii) a B-Raf kinase inhibitor, and
   (iii) a Wnt activator and/or a GSK-3 inhibitor,
   wherein the GMPs remain substantially morphologically unchanged after undergoing multiple cell passages and/or clonal expansion.

2. The method of claim 1, wherein the GMPs are derived or obtained from stem cells.

3. The method of claim 2, wherein the stem cells are genetically engineered prior to or during culturing.

4. The method of claim 2, wherein the stem cells are hematopoietic stem cells.

5. The method of claim 4, wherein the hematopoietic stem cells are isolated from the bone marrow of a subject.

6. The method of claim 5, wherein the subject is a mammalian subject.

7. The method of claim 1, wherein the culture medium comprises DMEM/F12 and Neural Basal Medium.

8. The method of claim 7, wherein the culture medium comprises DMEM/F12 and Neural Basal Medium in a ratio of about 5:1 to about 1:5.

9. The method of claim 8, wherein the culture medium comprises DMEM/F12 and Neural Basal Medium in a ratio of about 1:1.

10. The method of claim 1, wherein the culture medium comprises one or more supplements selected from insulin, transferrin, bovine serum albumin (BSA) fraction V, putrescine, sodium selenite, DL-α tocopherol, and/or linolenic acid.

11. The method of claim 10, wherein the culture medium is supplemented with insulin, transferrin, BSA fraction V, putrescine, sodium selenite, DL-α tocopherol, and linolenic acid.

12. The method of claim 1, wherein the growth factor is stem cell factor (SCF).

13. The method of claim 1, wherein the B-Raf kinase inhibitor is selected from the group consisting of GDC-0879, PLX4032, GSK2118436, BMS-908662, LGX818, PLX3603, RAF265, RO5185426, vemurafenib, PLX8394, SB590885 and any combination thereof.

14. The method of claim 1, wherein the Wnt activator is selected from the group consisting of SKL 2001, BML-284, WAY 262611, CAS 853220-52-7, QS11 and any combination thereof.

15. The method of claim 1, wherein the GSK-3 inhibitor is selected from the group consisting of CHIR99021, CHIR98014, SB216763, BIO, A1070722, AR-A014418 and any combination thereof.

16. The method of claim 1, further comprising differentiating the GMPs into macrophages comprising:
    culturing the GMPs with a macrophage differentiation medium comprising macrophage colony-stimulating factor (MCSF).

17. The method of claim 16, wherein the macrophage differentiation medium comprises RPMI 1640, fetal bovine serum (FBS) and MCSF.

18. The method of claim 1, further comprising differentiating the GMPs into granulocytes comprising:
    culturing the GMPs with a granulocyte differentiation medium comprising granulocyte colony-stimulating factor (GCSF).

19. The method of claim 18, wherein the granulocyte differentiation medium comprises RPMI 1640, FBS and GCSF.

20. A method to genetically modify granulocyte/macrophage progenitor (GMPs) cells, comprising:
    culturing GMPs according to the method of claim 1, and
    genetically engineering a modification into the GMPs, using a gene editing system, homologous recombination, or site directed mutagenesis.

21. The method of claim 20, wherein the genetically engineering modification comprises replacing or disrupting an existing gene, or altering a genetic locus to contain sequence information not found at the genetic locus.

22. The method of claim 21, wherein the genetically engineering modification of the GMPs comprises a knockout SIRPα and/or PI3Kγ gene.

* * * * *